US005922575A

United States Patent [19]

Cockerill, III et al.

[11] Patent Number: 5,922,575

[45] Date of Patent: *Jul. 13, 1999

[54] **MUTATIONS IN THE KATG GENE USEFUL FOR DETECTION OF *M. TUBERCULOSIS***

[75] Inventors: Franklin R. Cockerill, III; Bruce C. Kline; James R. Uhl, all of Rochester, Minn.

[73] Assignee: Mayo Foundation for Medical Education & Research, Rochester, Minn.

[ * ] Notice: This patent is subject to a terminal disclaimer.

[21] Appl. No.: 08/852,219

[22] Filed: May 7, 1997

Related U.S. Application Data

[63] Continuation-in-part of application No. 08/418,782, Apr. 7, 1995, Pat. No. 5,658,733, which is a continuation-in-part of application No. 08/228,662, Apr. 18, 1994, Pat. No. 5,688,639.

[51] Int. Cl.[6] .......................... C12P 19/34; C07H 21/04

[52] U.S. Cl. .......................... 435/91.2; 435/6; 435/91.1; 435/863; 536/23.1; 536/24.3; 536/24.33

[58] Field of Search .......................... 435/5, 6, 91.1, 435/91.2, 183, 863; 536/23.1, 24.3, 24.33, 25.3; 935/76, 8, 77, 78

[56] References Cited

U.S. PATENT DOCUMENTS

| | | | |
|---|---|---|---|
| 4,800,159 | 1/1989 | Mullis et al. | 435/172 |
| 5,658,733 | 8/1997 | Cockerill, III et al. | 435/6 |

FOREIGN PATENT DOCUMENTS

| | | | |
|---|---|---|---|
| 88/03957 | 2/1988 | WIPO | C12Q 1/68 |
| 93/22454 | 11/1993 | WIPO . | |
| WO 96/15267 | 5/1996 | WIPO . | |

OTHER PUBLICATIONS

Marttila et al., "katG Mutations in Isoniazid–Resistant *Mycobacterium tuberculosis* Isolates Recovered from Finnish Patients," *Antimicrobial Agents and Chemotherapy,* 40, 2187–2189 (1996).

Temesgen et al., "Use of polymerase chain reaction single–strand conformation polymorphism (PCR–SSCP) analysis to detect a point mutation in the catalase–peroxidase gene (katG) of *Mycobacterium tuberculosis," Molecular and Cellular Probes,* 11, 59–63 (1997).

"Amplicor™ *Mycobacterium Tuberculosis* Test", Product manual and Material Safety Data Sheets, Roche Diagnostic Systems, Inc., Branchburg, New Jersey, 26 pages, (1994).

"Amplified *Mycobacterium Tuberculosis* Direct Test", Product manual, Gen–Probe Incorporated, San Diego, California, 1–8, (1995).

"Sigma Molecular Biology Catalog", p. 54, (1989).

Chaisson, R.E., et al., "Tuberculosis in Patients with the Acquired Immunodeficiency Syndrome", *Am. Res. Resp. Dis.,* 136, 570–574 (1987).

Cockerill, III, F.R., et al., "Rapid Identification of a Point Mutation of the *Myobacterium tuberculosis* Catalase–Peroxidase (katG) Gene Associated with Isoniazid Resistance", *J. of Infectious Diseases, 171,* 240–245 (Jan. 1995).

Dooley, S.W., et al., "Multidrug–resistant Tuberculosis", *Ann. Int. Med.,* 117, 257 (Aug. 1, 1992).

Eisenach, K.D., et al., "Polymerase Chain Reaction Amplification of a Repetitive DNA Sequence Specific for *Mycobacterium tuberculosis", J. Infect. Dis.,* 161, No. 4, 997 (Apr. 1990).

Fischl, M.A., et al., "An Outbreak of Tuberculosis Caused by Multiple–drug–resistant Tubercle Bacilli among patients with HIV infection", *Ann. Int. Med.,* 117, 177 (Aug. 1, 1992).

Heym, B., et al., "Characterization of the katG Gene Encoding a Catalase–Peroxidase Required for the Isoniazid Susceptibility of *Mycobacterium tuberculosis", J. Bacteriol.,* 175, No. 13, 4255 (Jul. 1993).

Heym, B., et al., "Missense Mutations in the Catalase–Peroxidase Gene, katG, are associated with isoniazid resistance in *Mycobacterium tuberculosis", Molecular Biology, 15,* 235–245 (1995).

Middlebrook, G., ""Isoniazid–Resistance and Catalase Activity of Tubercle Bacilli"", *Am. Rev. Tuberc.,* 69, 471 (1954).

Miller, N., et al., "Evaluation of the Gen–Probe Amplified *Mycobacterium tuberculosis* Test (GPA–tb) and the Polymerase Chain Reaction (PCR) on patients with Pulmonary Tuberculosis", *Abstracts of the 93rd Meeting of the ASM,* Abstract No. U–48, Atlanta, GA, p. 177 (1993).

Pearson, M.L., et al., "Nosocimial Transmission of Multidrug–resistant *Mycobacterium tubercolosis.* A Risk to Patients and Health Care Workers",*Ann. Int. Med.,* 117, 191 (Aug. 1, 1992).

Snider, Jr., D.E., et al., "The New Tuberculosis", *New Engl. J. Med.,* 326, No. 10, 703 (1992).

Snider, D., "Research Towards Global Control and Prevention of Tuberculosis with an Emphasis on Vaccine Development", *Rev. Inf. Dis.,* vol. II, S336–337 (Mar./Apr. 1989).

Sommer, R., et al., "Minimal Homology Requirements for PCR Primers", *Nucleic Acids Research,* 17, 6749, (1989).

Takayama, K., et al., "Isonicotinic Acid Hydrazide", *Mechanism of Action of Antibacterial Agents,* Ed. F.E. Hahn, Springer–Verlag, at pp. 98–119 (1979).

Youatt, J., "A Review of the Action of Isoniazid", *Am. Rev. Respon. Dis.,* 99, 729 (1969).

Zhang, Y., et al., "The Catalase–Peroxide Gene and Isoniazid Resistance of *Mycobacterium tubercolosis", Nature, 358,* 591 (Aug. 13, 1992).

Zhang, Y., "Transformation with KatG restores isoniazid––sensitivity inmycobacterium tuberculosis isolates resistant to a range of drug concentrations", *Molec. Microbiol.,* 8(3), 521 (1993).

*Primary Examiner*—Bradley L. Sisson

*Attorney, Agent, or Firm*—Mueting, Raasch, & Gebhardt, P.A.

[57] ABSTRACT

A method for selectively detecting *M. tuberculosis* is provided employing restriction fragment length polymorphism analysis of an enzymatic digest of the *M. tuberculosis* katG gene.

22 Claims, 15 Drawing Sheets

```
  61 AGGAATGcTGTGcCCGAGCAACACCCACCCATtACAGAaaccaccaCCGG 110
     ||||||||||||||||||||||||||||||||||||||||||||||||||
1970 AGGAATGCTGTGCCCGAGCAACACCCACCCATTACAGAAACCACCACCGG 2019

 111 AGCCgCTAgCAACGgCTGTCCCGTCGTGGGTCATATGAAATACCCcgTCG 160
     ||||||||||||||||||||||||||||||||||||||||||||||||||
2020 AGCCGCTAGCAACGGCTGTCCCGTCGTGGGTCATATGAAATACCCCGTCG 2069

 161 AGGGCGGcGGAAACCAGGACTGGTGgcCCAACCGgCTCAATCTGAAGGTA 210
     ||||||||||||||||||||||||||||||||||||||||||||||||||
2070 AGGGCGGCGGAAACCAGGACTGGTGGCCCAACCGGCTCAATCTGAAGGTA 2119

 211 CTGCACCaAAACCCGgCCGTCGCTGAcCCGATGGGTGCGGCGTTCGACTA 260
     ||||||||||||||||||||||||||||||||||||||||||||||||||
2120 CTGCACCAAAACCCGGCCGTCGCTGACCCGATGGGTGCGGCGTTCGACTA 2169

 261 TgCCgCGGAGGTCGCGACCATCGACGTTGACgCCCTGACGCGGGACATCG 310
     ||||||||||||||||||||      ||||||||||||||||||||||||
2170 TGCCGCGGAGGTCGCGACCAGTCGACTTGACGCCCTGACGCGGGACATCG 2219

 311 AGGAAGTGATGACCACCTCGCAgCCGTGgTGGCCCgcCGACTACGGCCAC 360
     ||||||||||||||||||||||||||||||||||||||||||||||||||
2220 AGGAAGTGATGACCACCTCGCAGCCGTGGTGGCCCGCCGACTACGGCCAC 2269

 361 TACGGGCCGCTGTTTATCCGGATGGCGTGGCACGCTGCCGGCACCTACCG 410
     ||||||||||||||||||||||||||||||||||||||||||||||||||
2270 TACGGGCCGCTGTTTATCCGGATGGCGTGGCACGCTGCCGGCACCTACCG 2319

 411 CATCCACGACGGCCGCGGCGGCGCCGGGGGCGGCATgCAGCgGTTCGCGC 460
     ||||||||||||||||||||||||||||||||||||||||||||||||||
2320 CATCCACGACGGCCGCGGCGGCGCCGGGGGCGGCATGCAGCGGTTCGCGC 2369

 461 CGCTTAACAGCTGGCCCGACAACGCCAGCTTGGACAAGGCGCGCCGGcTG 510
     ||||||||||||||||||||||||||||||||||||||||||||||||||
2370 CGCTTAACAGCTGGCCCGACAACGCCAGCTTGGACAAGGCGCGCCGGCTG 2419

 511 CTGTGGCCGGTCAAGAAGAAGTACGGCAAGAAGCTCTCATGGGCGGACCT 560
     ||||||||||||||||||||||||||||||||||||||||||||||||||
2420 CTGTGGCCGGTCAAGAAGAAGTACGGCAAGAAGCTCTCATGGGCGGACCT 2469

 561 GATTGTTTTCgCCGgCAACTGC.GCGCT.GGAATCGATGGGCTTCAAGAC 608
     ||||||||||||||||||| || ||||| |||||||||||||||||||||
2470 GATTGTTTTCGCCGGCAACCGCTGCGCTCGGAATCGATGGGCTTCAAGAC 2519

 609 GTTCGGGTTCGGCTTCGGCCGGGTCGACCAGTGGGAGCCCGATGAGGTCT 658
     ||||||||||||||||||| | ||||||||||||||| ||||||||||||
2520 GTTCGGGTTCGGCTTCGG..GCGTCGACCAGTGGGAGACCGATGAGGTCT 2567

 659 ATTGGGGCAAGGAAGCCACCTGgCTCGGCGATGAGCGTTACAGCGGTAAG 708
     |||||||||||||||||||||||||||||||||||| ||||||||| |||||
2568 ATTGGGGCAAGGAAGCCACCTGGCTCGGCGATGACGGTTACAGC.GTAAG 2616
```

FIG. 1A

```
 709 CGGGATCTGGAGAACCCgCTGgCCGCGGTGcAGATGGGGCTGATCTACGT 758
     |  ||||||||||||||||||||||||||||||||||||||||||||||||
2617 C..GATCTGGAGAACCCGCTGGCCGCGGTGCAGATGGGGCTGATCTACGT 2664

 759 GaACCCGGAGGGGCCGAACGGCAACCCGGACCCCATGgCCGCGGCGGTCG 808
     ||||||||||| ||||||||||||||||||||||||||||||||||||||
2665 GAACCCGGAGGCGCCGAACGGCAACCCGGACCCCATGGCCGCGGCGGTCG 2714

 809 ACATTCGCGAGACGTTTCGGCGCATGGCCATGAaCGACGTCGAAACAgcG 858
     ||||||||||||||||||||||||||||||||||||||||||||||||||
2715 ACATTCGCGAGACGTTTCGGCGCATGGCCATGAACGACGTCGAAACAGCG 2764

 859 gcgCTGATCGTcGGCGGTCACACTTTCGGTAAGACCCATGGCgCCGGCCC 908
     ||||||||||||||||||||||||||||||||||||||||||||||||||
2765 GCGCTGATCGTCGGCGGTCACACTTTCGGTAAGACCCATGGCGCCGGCCC 2814

 909 GGcCGATCTGGTCGGCCCCGAACCCGAGGCTGCTCCGCTGGAGCAGATGG 958
     ||||||||||||||||||||||||||||||||||||||||||||||||||
2815 GGCCGATCTGGTCGGCCCCGAACCCGAGGCTGCTCCGCTGGAGCAGATGG 2864

 959 GCTTGGGCTGGAAGAGcTCGTATGgCACCGGAACCGGTAAGGACGCGATC 1008
     ||||||||||||||||||||||||||||||||||||||||||||||||||
2865 GCTTGGGCTGGAAGAGCTCGTATGGCACCGGAACCGGTAAGGACGCGATC 2914

1009 ACCAgCGGCATCGAGGTCGTATGGACGAACACCCCGACGAAATGGGACAA 1058
     ||||||||||||||||||||||||||||||||||||||||||||||||||
2915 ACCAGCGGCATCGAGGTCGTATGGACGAACACCCCGACGAAATGGGACAA 2964

1059 CAGTTTCCTCGAGATCCTGTaCGGCTACGAGTGGGAGCTGACGAAGAGCC 1108
     ||||||||||||||||||||||||||||||||||||||||||||||||||
2965 CAGTTTCCTCGAGATCCTGTACGGCTACGAGTGGGAGCTGACGAAGAGCC 3014

1109 CTGCTGGCGCTTGGCAATACACCGCCAAGGACGGCGCCGGTGCCGGCACC 1158
     ||||||||||||||||||||||||||||||||||||||||||||||||||
3015 CTGCTGGCGCTTGGCAATACACCGCCAAGGACGGCGCCGGTGCCGGCACC 3064

1159 ATCCCGGACCCGTTCGGcGGGCCAGGGCGCTCCCCGACGATGCTGGCCAC 1208
     ||||||||||||||||||||||||||||||||||||||||||||||||||
3065 ATCCCGGACCCGTTCGGCGGGCCAGGGCGCTCCCCGACGATGCTGGCCAC 3114

1209 TGACCTCTCGCTGCGGGTGGATCCGATCTATGAGCGGATCACGCGTCGCT 1258
     ||||||||||||||||||||||||||||||||||||||||||||||||||
3115 TGACCTCTCGCTGCGGGTGGATCCGATCTATGAGCGGATCACGCGTCGCT 3164

1259 GGCTGGAACACCCCGAGGAATTGGCCGACGAGTTCGCCAAGGCCTGGTAC 1308
     |||||||||||||||||||||||||||||||||||  |||||||||||||
3165 GGCTGGAACACCCCGAGGAATTGGCCGACGAGTTCCGCAAGGCCTGGTAC 3214

1309 AAGCTGATCCACCGAGACATGGgTCCCGtTGcGAGATACCTTGGGcCGcT 1358
     ||||||||||||||||||||||||||||||||||||||||||||||||||
3215 AAGCTGATCCACCGAGACATGGGTCCCGTTGCGAGATACCTTGGGCCGCT 3264
```

FIG. 1B

```
1359 GGTCCCCAAGcAGACCCTGcTGTGGcAGGATCCGGTCCCTGcGGTCAGCC 1408
     ||||||||||||||||||||||||||||||||||||||||||||||||| |
3265 GGTCCCCAAGCAGACCCTGCTGTGGCAGGATCCGGTCCCTGCGGTCAG.C 3313

1409 ACGAcCTCGTCGGcGAAGcCGAGATTGCCAGCCTTAAGAGCCAGATCCgG 1458
     ||||||||||||||||||  ||||||||||||||||||||||||||||
3314 ACGACCTCGTCGGCGAAGC..AGATTGCCAGCCTTAAGAGCCAGATCCGG 3361

1459 GCATCGGGATTGACTGTCTCACAGCTAGTTTCGACCGCATGGGCGGCGGC 1508
     ||||||||||||||||||||||||||||||||||||||||||||||||||
3362 GCATCGGGATTGACTGTCTCACAGCTAGTTTCGACCGCATGGGCGGCGGC 3411

1509 GTCGTCGTTCCGTGGTAGCGACAAgCGCGGcGGCGCCAACGGTGGTCGCA 1558
     ||||||||||||||||||||||||||||||||||||||||||||||||||
3412 GTCGTCGTTCCGTGGTAGCGACAAGCGCGGCGGCGCCAACGGTGGTCGCA 3461

1559 TCCgCCTGCAGCCACAAGTCGGGtGGGAGGTCAACGACCCCGACGGGGAT 1608
     |||||||||||||||||||||||||||||||||||||||||||   ||||
3462 TCCGCCTGCAGCCACAAGTCGGGTGGGAGGTCAACGACCCCGAC..GGAT 3509

1609 CTGCGCAAGGTCATTCGCACCCTGGAAGAGATCCAGGAGTCATTCAACTC 1658
     |||||||||||||||||||||| |||||||||||||||||||||
3510 CTGCGCAAGGTCATTCGCACCCT.GAAGAGATCCAGGAGTCATTCA.... 3554

1659 CGCGGCgCCGGGGAACATCAAAGTGTCCTTCGCCGACCTCGTCGTGCTCG 1708
     | ||||||  ||||||||||||||||||||||||||||||||||||||||
3555 CTCGGCGC..GGGAACATCAAAGTGTCCTTCGCCGACCTCGTCGTGCTCG 3602

1709 GTGGCTGTGcCgCCATAGAGAAAGCAgCAAAGGCGGCTGGCCACAACATC 1758
     ||||||||| | ||||||||||||||||||||||||||||||||||||||
3603 GTGGCTGTGCGCCACTAGAGAAAGCAGCAAAGGCGGCTGGCCACAACATC 3652

1759 ACGGTgCCCTTCACCCCGGGCCGcACGGATGCgTCGCAGGAACAAACCGA 1808
     |||||||||||||||||||||   ||||||||||||||||||||||||||
3653 ACGGTGCCCTTCACCCCGGGCCCGCACGATGCGTCGCAGGAACAAACCGA 3702

1809 CGTGGAATCCTTTGCCGTGCTGGAGcCCAAGGCAGATGGCTTCCGAAACT 1858
     ||||||||||||||||||||||||||||||||||||||||||||||||||
3703 CGTGGAATCCTTTGCCGTGCTGGAGCCCAAGGCAGATGGCTTCCGAAACT 3752

1859 ACCTCGGAAAGGGCAACCCGTTGCCGGCCGAGTACAT.gCTgcTCGACAA 1907
     ||||||||||||||| |||||||||||||||||||||  ||| |||||||
3753 ACCTCGGAAAGGGCAA.CCGTTGCCGGCCGAGTACATCGCTGCTCGACAA 3801

1908 GGCGAACCTGCTTACGCTCAGTgCCCCTGAGATGACGGTGCTGGTAGGTG 1957
     ||||||||||||||||||||||||||||||||||||||||||||||||||
3802 GGCGAACCTGCTTACGCTCAGTGCCCCTGAGATGACGGTGCTGGTAGGTG 3851

1958 GCCTGCGCGTCCTCGG.GCAAACTACAAGcGCTTACCGCTGGGCGTgTTC 2006
     ||||||||||||||||| |||||||||||||||||||||||||||||||||
3852 GCCTGCGCGTCCTCGGCGCAAACTACAAGCGCTTACCGCTGGGCGTGTTC 3901
```

FIG. 1C

```
2007 ACCGAGGCCTCCGAGTCACTGACCAACGACTTCTTCGTGAACCTGCTCGA 2056
     ||||||||||||||||||||||||||||||||||||||||||||||||||
3902 ACCGAGGCCTCCGAGTCACTGACCAACGACTTCTTCGTGAACCTGCTCGA 3951

2057 CATGGGTATCACCTGGGAGCCCTCGCCAGCAGATGaCGGgACCTACCAGG 2106
     ||||||||||||||||||||||||||||||||||||||||||||||||||
3952 CATGGGTATCACCTGGGAGCCCTCGCCAGCAGATGACGGGACCTACCAGG 4001

2107 GcAAGGATGGCAGTgGCAAGGTGAAGTGGACCGGcAGCCGCGTGGACCTG 2156
     ||||||||||||||||||||||||||||||||||||||||||||||||||
4002 GCAAGGATGGCAGTGGCAAGGTGAAGTGGACCGGCAGCCGCGTGGACCTG 4051

2157 gTCTTCGGgtCCAACTCGGAGTTGCGGGCGCTTGTCGAGGTCTATGGCGC 2206
     ||||||||||||||||||||||||||||||||||||||||||||| ||||
4052 GTCTTCGGGTCCAACTCGGAGTTGCGGGCGCTTGTCGAGGTCTAT.GCGC 4100

2207 CGATGACGC.GCAGCCGAAGTTCGTGCAGGACTTCGTCGCTGCCTGGgAC 2255
     ||||||||| |||| |||||||||||   |  ||||||||||| ||||||
4101 CGATGACGCGGCAGGCGAAGTTCGTGACAGGATTCGTCGCTGCGTGGGAC 4150

2256 AAGGTGATGAACCTCGACAGGTTCGACGTgCGCTGATTCG 2295
     ||||||||||||||||||||||||||||||||||||||||
4151 AAGGTGATGAACCTCGACAGGTTCGACGTGCGCTGATTCG 4190
```

FIG. 1D

| | | | | | |
|---|---|---|---|---|---|
| N | | 11 | 21 | 31 | 41 |
| 1 | VPEQHPPITE | TTTGAASNGC | PVVGHMKYPV | EGGGNQDWWP | NRLNLKVLHQ |
| N | | 61 | 71 | 81 | 91 |
| 51 | NPAVADPMGA | AFDYAAEVAT | IDVDALTRDI | EEVMTTSQPW | WPADYGHYGP |
| N | | 11 | 21 | 31 | 41 |
| 101 | LFIRMAWHAA | GTYRIHDGRG | GAGGGMQRFA | PLNSWPDNAS | LDKARRLLWP |
| N | | 61 | 71 | 81 | 91 |
| 151 | VKKKYGKKLS | WADLIVFAGN | CALESMGFKT | FGFGFGRVDQ | WEPDEVYWGK |
| N | | 11 | 21 | 31 | 41 |
| 201 | EATWLGDERY | SGKRDLENPL | AAVQMGLIYV | NPEGPNGNPD | PMAAAVDIRE |
| N | | 61 | 71 | 81 | 91 |
| 251 | TFRRMAMNDV | ETAALIVGGH | TFGKTHGAGP | ADLVGPEPEA | APLEQMGLGW |
| N | | 11 | 21 | 31 | 41 |
| 301 | KSSYGTGTGK | DAITSGIEVV | WTNTPTKWDN | SFLEILYGYE | WELTKSPAGA |
| N | | 61 | 71 | 81 | 91 |
| 351 | WQYTAKDGAG | AGTIPDPFGG | PGRSPTMLAT | DLSLRVDPIY | ERITRRWLEH |
| N | | 11 | 21 | 31 | 41 |
| 401 | PEELADEFAK | AWYKLIHRDM | GPVARYLGPL | VPKQTLLWQD | PVPAVSHDLV |
| N | | 61 | 71 | 81 | 91 |
| 451 | GEAEIASLKS | QIRASGLTVS | QLVSTAWAAA | SSFRGSDKRG | GANGGRIRLQ |
| N | | 11 | 21 | 31 | 41 |
| 501 | PQVGWEVNDP | DGDLRKVIRT | LEEIQESFNS | AAPGNIKVSF | ADLVVLGGCA |
| N | | 61 | 71 | 81 | 91 |
| 551 | AIEKAAKAAG | HNITVPFTPG | RTDASQEQTD | VESFAVLEPK | ADGFRNYLGK |
| N | | 11 | 21 | 31 | 41 |
| 601 | GNPLPAEYML | LDKANLLTLS | APEMTVLVGG | LRVLGANYKR | LPLGVFTEAS |
| N | | 61 | 71 | 81 | 91 |
| 651 | ESLTNDFFVN | LLDMGITWEP | SPADDGTYQG | KDGSGKVKWT | GSRVDLVFGS |
| N | | 11 | 21 | 31 | 41 |
| 701 | NSELRALVEV | YGADDAQPKF | VQDFVAAWDK | VMNLDRFDVR | & |

FIG. 2

```
          10                  30                  50
    CGATATCCGACACTTCGCGATCACATCCGTGATCACAGCCCGATAACACCAACTCCTGGA

          70                  90                  110
    AGGAATGCTGTGCCCGAGCAACACCCACCCATTACAGAAACCACCACCGGAGCCGCTAGC
1           V  P  E  Q  H  P  P  I  T  E  T  T  T  G  A  A  S     17

          130                 150                 170
    AACGGCTGTCCCGTCGTGGGTCATATGAAATACCCCGTCGAGGGCGGCGGAAACCAGGAC
18  N  G  C  P  V  V  G  H  M  K  Y  P  V  E  G  G  G  N  Q  D    37

          190                 210                 230
    TGGTGGCCCAACCGGCTCAATCTGAAGGTACTGCACCAAAACCCGGCCGTCGCTGACCCG
38  W  W  P  N  R  L  N  L  K  V  L  H  Q  N  P  A  V  A  D  P    57

          250                 270                 290
    ATGGGTGCGGCGTTCGACTATGCCGCGGAGGTCGCGACCATCGACGTTGACGCCCTGACG
58  M  G  A  A  F  D  Y  A  A  E  V  A  T  I  D  V  D  A  L  T    77

          310                 330                 350
    CGGGACATCGAGGAAGTGATGACCACCTCGCAGCCGTGGTGGCCCGCCGACTACGGCCAC
78  R  D  I  E  E  V  M  T  T  S  Q  P  W  W  P  A  D  Y  G  H    97

          370                 390                 410
    TACGGGCCGCTGTTTATCCGGATGGCGTGGCACGCTGCCGGCACCTACCGCATCCACGAC
98  Y  G  P  L  F  I  R  M  A  W  H  A  A  G  T  Y  R  I  H  D    117

          430                 450                 470
    GGCCGCGGCGGCGCCGGGGGCGGCATGCAGCGGTTCGCGCCGCTTAACAGCTGGCCCGAC
118 G  R  G  G  A  G  G  G  M  Q  R  F  A  P  L  N  S  W  P  D    137

          490                 510                 530
    AACGCCAGCTTGGACAAGGCGCGCCGGCTGCTGTGGCCGGTCAAGAAGAAGTACGGCAAG
138 N  A  S  L  D  K  A  R  R  L  L  W  P  V  K  K  K  Y  G  K    157

          550                 570                 590
    AAGCTCTCATGGGCGGACCTGATTGTTTTCGCCGGCAACTGCGCGCTGGAATCGATGGGC
158 K  L  S  W  A  D  L  I  V  F  A  G  N  C  A  L  E  S  M  G    177

          610                 630                 650
    TTCAAGACGTTCGGGTTCGGCTTCGGCCGGGTCGACCAGTGGGAGCCCGATGAGGTCTAT
178 F  K  T  F  G  F  G  F  G  R  V  D  Q  W  E  P  D  E  V  Y    197

          670                 690                 710
    TGGGGCAAGGAAGCCACCTGGCTCGGCGATGAGCGTTACAGCGGTAAGCGGGATCTGGAG
198 W  G  K  E  A  T  W  L  G  D  E  R  Y  S  G  K  R  D  L  E    217

          730                 750                 770
    AACCCGCTGGCCGCGGTGCAGATGGGGCTGATCTACGTGAACCCGGAGGGGCCGAACGGC
218 N  P  L  A  A  V  Q  M  G  L  I  Y  V  N  P  E  G  P  N  G    237

          790                 810                 830
    AACCCGGACCCCATGGCCGCGGCGGTCGACATTCGCGAGACGTTTCGGCGCATGGCCATG
238 N  P  D  P  M  A  A  A  V  D  I  R  E  T  F  R  R  M  A  M    257

          850                 870                 890
    AACGACGTCGAAACAGCGGCGCTGATCGTCGGCGGTCACACTTTCGGTAAGACCCATGGC
258 N  D  V  E  T  A  A  L  I  V  G  G  H  T  F  G  K  T  H  G    277
```

FIG. 7A 910 930 950
GCCGGCCCGGCCGATCTGGTCGGCCCCGAACCCGAGGCTGCTCCGCTGGAGCAGATGGGC
278 A G P A D L V G P E P E A A P L E Q M G 297

970 990 1010
TTGGGCTGGAAGAGCTCGTATGGCACCGGAACCGGTAAGGACGCGATCACCAGCGGCATC
298 L G W K S S Y G T G T G K D A I T S G I 317

1030 1050 1070
GAGGTCGTATGGACGAACACCCCGACGAAATGGGACAACAGTTTCCTCGAGATCCTGTAC
318 E V V W T N T P T K W D N S F L E I L Y 337

1090 1110 1130
GGCTACGAGTGGGAGCTGACGAAGAGCCCTGCTGGCGCTTGGCAATACACCGCCAAGGAC
338 G Y E W E L T K S P A G A W Q Y T A K D 357

1150 1170 1190
GGCGCCGGTGCCGGCACCATCCCGGACCCGTTCGGCGGGCCAGGGCGCTCCCCGACGATG
358 G A G A G T I P D P F G G P G R S P T M 377

1210 1230 1250
CTGGCCACTGACCTCTCGCTGCGGGTGGATCCGATCTATGAGCGGATCACGCGTCGCTGG
378 L A T D L S L R V D P I Y E R I T R R W 397

1270 1290 1310
CTGGAACACCCCGAGGAATTGGCCGACGAGTTCGCCAAGGCCTGGTACAAGCTGATCCAC
398 L E H P E E L A D E F A K A W Y K L I H 417

1330 1350 1370
CGAGACATGGGTCCCGTTGCGAGATACCTTGGGCCGCTGGTCCCCAAGCAGACCCTGCTG
418 R D M G P V A R Y L G P L V P K Q T L L 437

1390 1410 1430
TGGCAGGATCCGGTCCCTGCGGTCAGCCACGACCTCGTCGGCGAAGCCGAGATTGCCAGC
438 W Q D P V P A V S H D L V G E A E I A S 457

1450 1470 1490
CTTAAGAGCCAGATCCGGGCATCGGGATTGACTGTCTCACAGCTAGTTTCGACCGCATGG
458 L K S Q I R A S G L T V S Q L V S T A W 477

1510 1530 1550
GCGGCGGCGTCGTCGTTCCGTGGTAGCGACAAGCGCGGCGGCGCCAACGGTGGTCGCATC
478 A A A S S F R G S D K R G G A N G G R I 497

1570 1590 1610
CGCCTGCAGCCACAAGTCGGGTGGGAGGTCAACGACCCCGACGGGGATCTGCGCAAGGTC
498 R L Q P Q V G W E V N D P D G D L R K V 517

1630 1650 1670
ATTCGCACCCTGGAAGAGATCCAGGAGTCATTCAACTCCGCGGCGCCGGGGAACATCAAA
518 I R T L E E I Q E S F N S A A P G N I K 537

1690 1710 1730
GTGTCCTTCGCCGACCTCGTCGTGCTCGGTGGCTGTGCCGCCATAGAGAAAGCAGCAAAG
538 V S F A D L V V L G G C A A I E K A A K 557

FIG. 7B

```
           1750                1770                1790
    GCGGCTGGCCACAACATCACGGTGCCCTTCACCCCGGGCCGCACGGATGCGTCGCAGGAA
558 A  A  G  H  N  I  T  V  P  F  T  P  G  R  T  D  A  S  Q  E    577

           1810                1830                1850
    CAAACCGACGTGGAATCCTTTGCCGTGCTGGAGCCCAAGGCAGATGGCTTCCGAAACTAC
578 Q  T  D  V  E  S  F  A  V  L  E  P  K  A  D  G  F  R  N  Y    597

           1870                1890                1910
    CTCGGAAAGGGCAACCCGTTGCCGGCCGAGTACATGCTGCTCGACAAGGCGAACCTGCTT
598 L  G  K  G  N  P  L  P  A  E  Y  M  L  L  D  K  A  N  L  L    617

           1930                1950                1970
    ACGCTCAGTGCCCCTGAGATGACGGTGCTGGTAGGTGGCCTGCGCGTCCTCGGCGCAAAC
618 T  L  S  A  P  E  M  T  V  L  V  G  G  L  R  V  L  G  A  N    637

           1990                2010                2030
    TACAAGCGCTTACCGCTGGGCGTGTTCACCGAGGCCTCCGAGTCACTGACCAACGACTTC
638 Y  K  R  L  P  L  G  V  F  T  E  A  S  E  S  L  T  N  D  F    657

           2050                2070                2090
    TTCGTGAACCTGCTCGACATGGGTATCACCTGGGAGCCCTCGCCAGCAGATGACGGGACC
658 F  V  N  L  L  D  M  G  I  T  W  E  P  S  P  A  D  D  G  T    677

           2110                2130                2150
    TACCAGGGCAAGGATGGCAGTGGCAAGGTGAAGTGGACCGGCAGCCGCGTGGACCTGGTC
678 Y  Q  G  K  D  G  S  G  K  V  K  W  T  G  S  R  V  D  L  V    697

           2170                2190                2210
    TTCGGGTCCAACTCGGAGTTGCGGGCGCTTGTCGAGGTCTATGGCGCCGATGACGCGCAG
698 F  G  S  N  S  E  L  R  A  L  V  E  V  Y  G  A  D  D  A  Q    717

           2230                2250                2270
    CCGAAGTTCGTGCAGGACTTCGTCGCTGCCTGGGACAAGGTGATGAACCTCGACAGGTTC
718 P  K  F  V  Q  D  F  V  A  A  W  D  K  V  M  N  L  D  R  F    737

           2290                2310                2330
    GACGTGCGCTGATTCGGGTTGATCGGCCCTGCCCGCCGATCAACCACAACC
738 D  V  R  *                                                   740
```

FIG. 7C

RFLP analysis of M. tuberculosis katG mutations in codons 315 and 463.

4% Metaphor agarose (FMC), 1X TBE, 100 V

A&T = MW markers
B-S = MspI digests of PCR products (katG 904-1523)

| | |
|---|---|
| C,D,F,G,H,K,L,N,Q | wild genotype at codons 315 and 463 |
| M,O | RFLP indicating a mutation at codon 315 |
| E,I,P | RFLP indicating a mutation at codon 463 |
| B,J | RFLP indicating mutations at codons 315 and 463 |

RFLP (RsaI) analysis of *M. tuberculosis* katG mutations in codon 337.

8% PA, 200V, 20 min., EtBr stained

A-F RsaI digest of katG (904-1523) PCR products
G Blank
H MWM

A,B,D,E,F Wild genotype at codon 337
C RFLP indicating mutation at codon 337

RFLP (CfoI) analysis of *M. tuberculosis* katG mutations in codon 264

6% PA, 200V, 20 min., EtBr stained

| | |
|---|---|
| A,B,C,E | CfoI digest of katG (633-983) PCR product |
| | MWM |
| A,B,C | Wild genotype at codon 264 |
| E | RFLP indicating mutation at codon 264 |

SEQUENCE LISTING

```
(1) GENERAL INFORMATION:

   (iii) NUMBER OF SEQUENCES: 22


(2) INFORMATION FOR SEQ ID NO:1:

     (i) SEQUENCE CHARACTERISTICS:
          (A) LENGTH: 2235 base pairs
          (B) TYPE: nucleic acid
```

-continued (C) STRANDEDNESS: single
(D) TOPOLOGY: linear (ii) MOLECULE TYPE: DNA (xi) SEQUENCE DESCRIPTION: SEQ ID NO:1:

```
AGGAATGCTG TGCCCGAGCA ACACCCACCC ATTACAGAAA CCACCACCGG AGCCGCTAGC     60
AACGGCTGTC CCGTCGTGGG TCATATGAAA TACCCCGTCG AGGGCGGCGG AAACCAGGAC    120
TGGTGGCCCA ACCGGCTCAA TCTGAAGGTA CTGCACCAAA ACCCGGCCGT CGCTGACCCG    180
ATGGGTGCGG CGTTCGACTA TGCCGCGGAG GTCGCGACCA TCGACGTTGA CGCCCTGACG    240
CGGGACATCG AGGAAGTGAT GACCACCTCG CAGCCGTGGT GGCCCGCCGA CTACGGCCAC    300
TACGGGCCGC TGTTTATCCG GATGGCGTGG CACGCTGCCG GCACCTACCG CATCCACGAC    360
GGCCGCGGCG GCGCCGGGGG CGGCATGCAG CGGTTCGCGC CGCTTAACAG CTGGCCCGAC    420
AACGCCAGCT TGGACAAGGC GCGCCGGCTG CTGTGGCCGG TCAAGAAGAA GTACGGCAAG    480
AAGCTCTCAT GGGCGGACCT GATTGTTTTC GCCGGCAACT GCGCGCTGGA ATCGATGGGC    540
TTCAAGACGT TCGGGTTCGG CTTCGGCCGG GTCGACCAGT GGGAGCCCGA TGAGGTCTAT    600
TGGGGCAAGG AAGCCACCTG GCTCGGCGAT GAGCGTTACA GCGGTAAGCG GGATCTGGAG    660
AACCCGCTGG CCGCGGTGCA GATGGGGCTG ATCTACGTGA ACCCGGAGGG GCCGAACGGC    720
AACCCGGACC CCATGGCCGC GGCGGTCGAC ATTCGCGAGA CGTTTCGGCG CATGGCCATG    780
AACGACGTCG AAACAGCGGC GCTGATCGTC GGCGGTCACA CTTTCGGTAA GACCCATGGC    840
GCCGGCCCGG CCGATCTGGT CGGCCCCGAA CCCGAGGCTG CTCCGCTGGA GCAGATGGGC    900
TTGGGCTGGA AGAGCTCGTA TGGCACCGGA ACCGGTAAGG ACGCGATCAC CAGCGGCATC    960
GAGGTCGTAT GGACGAACAC CCCGACGAAA TGGGACAACA GTTTCCTCGA GATCCTGTAC   1020
GGCTACGAGT GGGAGCTGAC GAAGAGCCCT GCTGGCGCTT GGCAATACAC CGCCAAGGAC   1080
GGCGCCGGTG CCGGCACCAT CCCGGACCCG TTCGGCGGGC CAGGGCGCTC CCCGACGATG   1140
CTGGCCACTG ACCTCTCGCT GCGGGTGGAT CCGATCTATG AGCGGATCAC GCGTCGCTGG   1200
CTGGAACACC CCGAGGAATT GGCCGACGAG TTCGCCAAGG CCTGGTACAA GCTGATCCAC   1260
CGAGACATGG GTCCCGTTGC GAGATACCTT GGGCCGCTGG TCCCCAAGCA GACCCTGCTG   1320
TGGCAGGATC CGGTCCCTGC GGTCAGCCAC GACCTCGTCG GCGAAGCCGA GATTGCCAGC   1380
CTTAAGAGCC AGATCCGGGC ATCGGGATTG ACTGTCTCAC AGCTAGTTTC GACCGCATGG   1440
GCGGCGGCGT CGTCGTTCCG TGGTAGCGAC AAGCGCGGCG GCGCCAACGG TGGTCGCATC   1500
CGCCTGCAGC CACAAGTCGG GTGGGAGGTC AACGACCCCG ACGGGGATCT GCGCAAGGTC   1560
ATTCGCACCC TGGAAGAGAT CCAGGAGTCA TTCAACTCCG CGGCGCCGGG GAACATCAAA   1620
GTGTCCTTCG CCGACCTCGT CGTGCTCGGT GGCTGTGCCG CCATAGAGAA AGCAGCAAAG   1680
GCGGCTGGCC ACAACATCAC GGTGCCCTTC ACCCCGGGCC GCACGGATGC GTCGCAGGAA   1740
CAAACCGACG TGGAATCCTT TGCCGTGCTG GAGCCCAAGG CAGATGGCTT CCGAAACTAC   1800
CTCGGAAAGG GCAACCCGTT GCCGGCCGAG TACATGCTGC TCGACAAGGC GAACCTGCTT   1860
ACGCTCAGTG CCCCTGAGAT GACGGTGCTG GTAGGTGGCC TGCGCGTCCT CGGGCAAACT   1920
ACAAGCGCTT ACCGCTGGGC GTGTTCACCG AGGCCTCCGA GTCACTGACC AACGACTTCT   1980
TCGTGAACCT GCTCGACATG GGTATCACCT GGGAGCCCTC GCCAGCAGAT GACGGGACCT   2040
ACCAGGGCAA GGATGGCAGT GGCAAGGTGA AGTGGACCGG CAGCCGCGTG GACCTGGTCT   2100
TCGGGTCCAA CTCGGAGTTG CGGGCGCTTG TCGAGGTCTA TGGCGCCGAT GACGCGCAGC   2160
CGAAGTTCGT GCAGGACTTC GTCGCTGCCT GGGACAAGGT GATGAACCTC GACAGGTTCG   2220
```

-continued

ACGTGCGCTG ATTCG 2235

(2) INFORMATION FOR SEQ ID NO:2:

(i) SEQUENCE CHARACTERISTICS:
(A) LENGTH: 2221 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:2:

AGGAATGCTG TGCCCGAGCA ACACCCACCC ATTACAGAAA CCACCACCGG AGCCGCTAGC 60

AACGGCTGTC CCGTCGTGGG TCATATGAAA TACCCCGTCG AGGGCGGCGG AAACCAGGAC 120

TGGTGGCCCA ACCGGCTCAA TCTGAAGGTA CTGCACCAAA ACCCGGCCGT CGCTGACCCG 180

ATGGGTGCGG CGTTCGACTA TGCCGCGGAG GTCGCGACCA GTCGACTTGA CGCCCTGACG 240

CGGGACATCG AGGAAGTGAT GACCACCTCG CAGCCGTGGT GGCCCGCCGA CTACGGCCAC 300

TACGGGCCGC TGTTTATCCG GATGGCGTGG CACGCTGCCG GCACCTACCG CATCCACGAC 360

GGCCGCGGCG GCGCCGGGGG CGGCATGCAG CGGTTCGCGC CGCTTAACAG CTGGCCCGAC 420

AACGCCAGCT TGGACAAGGC GCGCCGGCTG CTGTGGCCGG TCAAGAAGAA GTACGGCAAG 480

AAGCTCTCAT GGGCGGACCT GATTGTTTTC GCCGGCAACC GCTGCGCTCG GAATCGATGG 540

GCTTCAAGAC GTTCGGGTTC GGCTTCGGGC GTCGACCAGT GGGAGACCGA TGAGGTCTAT 600

TGGGGCAAGG AAGCCACCTG GCTCGGCGAT GACGGTTACA GCGTAAGCGA TCTGGAGAAC 660

CCGCTGGCCG CGGTGCAGAT GGGGCTGATC TACGTGAACC CGGAGGCGCC GAACGGCAAC 720

CCGGACCCCA TGGCCGCGGC GGTCGACATT CGCGAGACGT TTCGGCGCAT GGCCATGAAC 780

GACGTCGAAA CAGCGGCGCT GATCGTCGGC GGTCACACTT TCGGTAAGAC CCATGGCGCC 840

GGCCCGGCCG ATCTGGTCGG CCCCGAACCC GAGGCTGCTC CGCTGGAGCA GATGGGCTTG 900

GGCTGGAAGA GCTCGTATGG CACCGGAACC GGTAAGGACG CGATCACCAG CGGCATCGAG 960

GTCGTATGGA CGAACACCCC GACGAAATGG GACAACAGTT TCCTCGAGAT CCTGTACGGC 1020

TACGAGTGGG AGCTGACGAA GAGCCCTGCT GGCGCTTGGC AATACACCGC CAAGGACGGC 1080

GCCGGTGCCG GCACCATCCC GGACCCGTTC GGCGGGCCAG GGCGCTCCCC GACGATGCTG 1140

GCCACTGACC TCTCGCTGCG GGTGGATCCG ATCTATGAGC GGATCACGCG TCGCTGGCTG 1200

GAACACCCCG AGGAATTGGC CGACGAGTTC CGCAAGGCCT GGTACAAGCT GATCCACCGA 1260

GACATGGGTC CCGTTGCGAG ATACCTTGGG CCGCTGGTCC CCAAGCAGAC CCTGCTGTGG 1320

CAGGATCCGG TCCCTGCGGT CAGCACGACC TCGTCGGCGA AGCAGATTGC CAGCCTTAAG 1380

AGCCAGATCC GGGCATCGGG ATTGACTGTC TCACAGCTAG TTTCGACCGC ATGGGCGGCG 1440

GCGTCGTCGT TCCGTGGTAG CGACAAGCGC GGCGGCGCCA ACGGTGGTCG CATCCGCCTG 1500

CAGCCACAAG TCGGGTGGGA GGTCAACGAC CCCGACGGAT CTGCGCAAGG TCATTCGCAC 1560

CCTGAAGAGA TCCAGGAGTC ATTCACTCGG CGCGGGAACA TCAAAGTGTC CTTCGCCGAC 1620

CTCGTCGTGC TCGGTGGCTG TGCGCCACTA GAGAAAGCAG CAAAGGCGGC TGGCCACAAC 1680

ATCACGGTGC CCTTCACCCC GGGCCCGCAC GATGCGTCGC AGGAACAAAC CGACGTGGAA 1740

TCCTTTGCCG TGCTGGAGCC CAAGGCAGAT GGCTTCCGAA ACTACCTCGG AAAGGGCAAC 1800

CGTTGCCGGC CGAGTACATC GCTGCTCGAC AAGGCGAACC TGCTTACGCT CAGTGCCCCT 1860

GAGATGACGG TGCTGGTAGG TGGCCTGCGC GTCCTCGGCG CAAACTACAA GCGCTTACCG 1920

-continued

```
CTGGGCGTGT TCACCGAGGC CTCCGAGTCA CTGACCAACG ACTTCTTCGT GAACCTGCTC   1980

GACATGGGTA TCACCTGGGA GCCCTCGCCA GCAGATGACG GGACCTACCA GGGCAAGGAT   2040

GGCAGTGGCA AGGTGAAGTG GACCGGCAGC CGCGTGGACC TGGTCTTCGG GTCCAACTCG   2100

GAGTTGCGGG CGCTTGTCGA GGTCTATGCG CCGATGACGC GGCAGGCGAA GTTCGTGACA   2160

GGATTCGTCG CTGCGTGGGA CAAGGTGATG AACCTCGACA GGTTCGACGT GCGCTGATTC   2220

G                                                                   2221
```

(2) INFORMATION FOR SEQ ID NO:3:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

```
TCGGACCATA ACGGCTTCCT GTTGGACGAG                                      30
```

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

```
AATCTGCTTC GCCGACGAGG TCGTGCTGAC                                      30
```

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

```
CACCCCGACG AAATGGGACA ACAGTTTCCT                                      30
```

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

```
GGGTCTGACA AATCGCGCCG GGCAAACACC                                      30
```

(2) INFORMATION FOR SEQ ID NO:7:

(i) SEQUENCE CHARACTERISTICS:
(A) LENGTH: 740 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:7:

```
Val Pro Glu Gly His Pro Pro Ile Thr Glu Thr Thr Thr Gly Ala Ala
1               5                   10                  15

Ser Asn Gly Cys Pro Val Val Gly His Met Lys Tyr Pro Val Glu Gly
            20                  25                  30

Gly Gly Asn Gln Asp Trp Trp Pro Asn Arg Leu Asn Leu Lys Val Leu
        35                  40                  45

His Gln Asn Pro Ala Val Ala Asp Pro Met Gly Ala Ala Phe Asp Tyr
    50                  55                  60

Ala Ala Glu Val Ala Thr Ile Asp Val Asp Ala Leu Thr Arg Asp Ile
65                  70                  75                  80

Glu Glu Val Met Thr Thr Ser Gln Pro Trp Trp Pro Ala Asp Tyr Gly
                85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Gly Met Gln Arg
        115                 120                 125

Phe Ala Pro Leu Asn Ser Trp Pro Asp Asn Ala Ser Leu Asp Lys Ala
    130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270

Gly Lys Thr His Gly Ala Gly Pro Ala Asp Leu Val Gly Pro Glu Pro
        275                 280                 285

Glu Ala Ala Pro Leu Glu Gln Met Gly Leu Gly Trp Lys Ser Ser Tyr
    290                 295                 300

Gly Thr Gly Thr Gly Lys Asp Ala Ile Thr Ser Gly Ile Glu Val Val
305                 310                 315                 320

Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365

Gly Gly Pro Gly Arg Ser Pro Thr Met Leu Ala Thr Asp Leu Ser Leu
    370                 375                 380

Arg Val Asp Pro Ile Tyr Glu Arg Ile Thr Arg Arg Trp Leu Glu His
385                 390                 395                 400
```

-continued

```
Pro Glu Glu Leu Ala Asp Glu Phe Ala Lys Ala Trp Tyr Lys Leu Ile
                405                 410                 415

His Arg Asp Met Gly Pro Val Ala Arg Tyr Leu Gly Pro Leu Val Pro
            420                 425                 430

Lys Gln Thr Leu Leu Trp Gln Asp Pro Val Pro Ala Val Ser His Asp
        435                 440                 445

Leu Val Gly Glu Ala Glu Ile Ala Ser Leu Lys Ser Gln Ile Arg Ala
    450                 455                 460

Ser Gly Leu Thr Val Ser Gln Leu Val Ser Thr Ala Trp Ala Ala Ala
465                 470                 475                 480

Ser Ser Phe Arg Gly Ser Asp Lys Arg Gly Gly Ala Asn Gly Gly Arg
                485                 490                 495

Ile Arg Leu Gln Pro Gln Val Gly Trp Glu Val Asn Asp Pro Asp Gly
            500                 505                 510

Asp Leu Arg Lys Val Ile Arg Thr Leu Glu Glu Ile Gln Glu Ser Phe
        515                 520                 525

Asn Ser Ala Ala Pro Gly Asn Ile Lys Val Ser Phe Ala Asp Leu Val
    530                 535                 540

Val Leu Gly Gly Cys Ala Ala Ile Glu Lys Ala Ala Lys Ala Ala Gly
545                 550                 555                 560

His Asn Ile Thr Val Pro Phe Thr Pro Gly Arg Thr Asp Ala Ser Gln
                565                 570                 575

Glu Gln Thr Asp Val Glu Ser Phe Ala Val Leu Glu Pro Lys Ala Asp
            580                 585                 590

Gly Phe Arg Asn Tyr Leu Gly Lys Gly Asn Pro Leu Pro Ala Glu Tyr
        595                 600                 605

Met Leu Leu Asp Lys Ala Asn Leu Leu Thr Leu Ser Ala Pro Glu Met
    610                 615                 620

Thr Val Leu Val Gly Gly Leu Arg Val Leu Gly Ala Asn Tyr Lys Arg
625                 630                 635                 640

Leu Pro Leu Gly Val Phe Thr Glu Ala Ser Glu Ser Leu Thr Asn Asp
                645                 650                 655

Phe Phe Val Asn Leu Leu Asp Met Gly Ile Thr Trp Glu Pro Ser Pro
            660                 665                 670

Ala Asp Asp Gly Thr Tyr Gln Gly Lys Asp Gly Ser Gly Lys Val Lys
        675                 680                 685

Trp Thr Gly Ser Arg Val Asp Leu Val Phe Gly Ser Asn Ser Glu Leu
    690                 695                 700

Arg Ala Leu Val Glu Val Tyr Gly Ala Asp Asp Ala Gln Pro Lys Phe
705                 710                 715                 720

Val Gln Asp Phe Val Ala Ala Trp Asp Lys Val Met Asn Leu Asp Arg
                725                 730                 735

Phe Asp Val Arg
            740
```

(2) INFORMATION FOR SEQ ID NO:8:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

```
GTCGAAACAG CGGCGCTGAT CGTCGGC                                      27
```

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

GTCGAAACAG CGACGCTGAT CGTCGGC 27

(2) INFORMATION FOR SEQ ID NO:10:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

CTCGAGATCC TGTACGGCTA CGAGTGG 27

(2) INFORMATION FOR SEQ ID NO:11:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

CTCGAGATCC TGTGCGGCTA CGAGTGG 27

(2) INFORMATION FOR SEQ ID NO:12:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

GACGCGATCA CCAGCGGCAT CGAGGTC 27

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

GACGCGATCA CCACCGGCAT CGAGGTC 27

(2) INFORMATION FOR SEQ ID NO:14:

(i) SEQUENCE CHARACTERISTICS:

-continued (A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

AAGAGCCAGA TCCGGGCATC GGGATTG 27

(2) INFORMATION FOR SEQ ID NO:15:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

AAGAGCCAGA TCCTGGCATC GGGATTG 27

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:16:

AGCTCGTATG GCACCGGAAC 20

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:17:

TTGACCTCCC ACCCGACTTG 20

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:18:

CGGTAAGCGG GATCTGGAGA 20

(2) INFORMATION FOR SEQ ID NO:19:

(i) SEQUENCE CHARACTERISTICS:
(A) LENGTH: 20 base pairs
(B) TYPE: nucleic acid
(C) STRANDEDNESS: single
(D) TOPOLOGY: linear

```
    (ii) MOLECULE TYPE: DNA

    (xi) SEQUENCE DESCRIPTION: SEQ ID NO:19:

CATTTCGTCG GGGTGTTCGT                                                  20


(2) INFORMATION FOR SEQ ID NO:20:

     (i) SEQUENCE CHARACTERISTICS:
          (A) LENGTH: 2331 base pairs
          (B) TYPE: nucleic acid
          (C) STRANDEDNESS: single
          (D) TOPOLOGY: linear

    (ii) MOLECULE TYPE: DNA

    (ix) FEATURE:
          (A) NAME/KEY: CDS
          (B) LOCATION: 70..2289

    (xi) SEQUENCE DESCRIPTION: SEQ ID NO:20:

CGATATCCGA CACTTCGCGA TCACATCCGT GATCACAGCC CGATAACACC AACTCCTGGA      60

AGGAATGCT GTG CCC GAG CAA CAC CCA CCC ATT ACA GAA ACC ACC ACC         108
          Val Pro Glu Gln His Pro Pro Ile Thr Glu Thr Thr Thr
            1               5                  10

GGA GCC GCT AGC AAC GGC TGT CCC GTC GTG GGT CAT ATG AAA TAC CCC       156
Gly Ala Ala Ser Asn Gly Cys Pro Val Val Gly His Met Lys Tyr Pro
     15                  20                  25

GTC GAG GGC GGC GGA AAC CAG GAC TGG TGG CCC AAC CGG CTC AAT CTG       204
Val Glu Gly Gly Gly Asn Gln Asp Trp Trp Pro Asn Arg Leu Asn Leu
 30                  35                  40                  45

AAG GTA CTG CAC CAA AAC CCG GCC GTC GCT GAC CCG ATG GGT GCG GCG       252
Lys Val Leu His Gln Asn Pro Ala Val Ala Asp Pro Met Gly Ala Ala
                 50                  55                  60

TTC GAC TAT GCC GCG GAG GTC GCG ACC ATC GAC GTT GAC GCC CTG ACG       300
Phe Asp Tyr Ala Ala Glu Val Ala Thr Ile Asp Val Asp Ala Leu Thr
             65                  70                  75

CGG GAC ATC GAG GAA GTG ATG ACC ACC TCG CAG CCG TGG TGG CCC GCC       348
Arg Asp Ile Glu Glu Val Met Thr Thr Ser Gln Pro Trp Trp Pro Ala
         80                  85                  90

GAC TAC GGC CAC TAC GGG CCG CTG TTT ATC CGG ATG GCG TGG CAC GCT       396
Asp Tyr Gly His Tyr Gly Pro Leu Phe Ile Arg Met Ala Trp His Ala
     95                 100                 105

GCC GGC ACC TAC CGC ATC CAC GAC GGC CGC GGC GGC GCC GGG GGC GGC       444
Ala Gly Thr Tyr Arg Ile His Asp Gly Arg Gly Gly Ala Gly Gly Gly
110                 115                 120                 125

ATG CAG CGG TTC GCG CCG CTT AAC AGC TGG CCC GAC AAC GCC AGC TTG       492
Met Gln Arg Phe Ala Pro Leu Asn Ser Trp Pro Asp Asn Ala Ser Leu
                130                 135                 140

GAC AAG GCG CGC CGG CTG CTG TGG CCG GTC AAG AAG AAG TAC GGC AAG       540
Asp Lys Ala Arg Arg Leu Leu Trp Pro Val Lys Lys Lys Tyr Gly Lys
            145                 150                 155

AAG CTC TCA TGG GCG GAC CTG ATT GTT TTC GCC GGC AAC TGC GCG CTG       588
Lys Leu Ser Trp Ala Asp Leu Ile Val Phe Ala Gly Asn Cys Ala Leu
        160                 165                 170

GAA TCG ATG GGC TTC AAG ACG TTC GGG TTC GGC TTC GGC CGG GTC GAC       636
Glu Ser Met Gly Phe Lys Thr Phe Gly Phe Gly Phe Gly Arg Val Asp
    175                 180                 185

CAG TGG GAG CCC GAT GAG GTC TAT TGG GGC AAG GAA GCC ACC TGG CTC       684
Gln Trp Glu Pro Asp Glu Val Tyr Trp Gly Lys Glu Ala Thr Trp Leu
190                 195                 200                 205

GGC GAT GAG CGT TAC AGC GGT AAG CGG GAT CTG GAG AAC CCG CTG GCC       732
Gly Asp Glu Arg Tyr Ser Gly Lys Arg Asp Leu Glu Asn Pro Leu Ala
                210                 215                 220
```

-continued

```
GCG GTG CAG ATG GGG CTG ATC TAC GTG AAC CCG GAG GGG CCG AAC GGC      780
Ala Val Gln Met Gly Leu Ile Tyr Val Asn Pro Glu Gly Pro Asn Gly
            225                 230                 235

AAC CCG GAC CCC ATG GCC GCG GCG GTC GAC ATT CGC GAG ACG TTT CGG      828
Asn Pro Asp Pro Met Ala Ala Ala Val Asp Ile Arg Glu Thr Phe Arg
        240                 245                 250

CGC ATG GCC ATG AAC GAC GTC GAA ACA GCG GCG CTG ATC GTC GGC GGT      876
Arg Met Ala Met Asn Asp Val Glu Thr Ala Ala Leu Ile Val Gly Gly
    255                 260                 265

CAC ACT TTC GGT AAG ACC CAT GGC GCC GGC CCG GCC GAT CTG GTC GGC      924
His Thr Phe Gly Lys Thr His Gly Ala Gly Pro Ala Asp Leu Val Gly
270                 275                 280                 285

CCC GAA CCC GAG GCT GCT CCG CTG GAG CAG ATG GGC TTG GGC TGG AAG      972
Pro Glu Pro Glu Ala Ala Pro Leu Glu Gln Met Gly Leu Gly Trp Lys
                290                 295                 300

AGC TCG TAT GGC ACC GGA ACC GGT AAG GAC GCG ATC ACC AGC GGC ATC     1020
Ser Ser Tyr Gly Thr Gly Thr Gly Lys Asp Ala Ile Thr Ser Gly Ile
            305                 310                 315

GAG GTC GTA TGG ACG AAC ACC CCG ACG AAA TGG GAC AAC AGT TTC CTC     1068
Glu Val Val Trp Thr Asn Thr Pro Thr Lys Trp Asp Asn Ser Phe Leu
        320                 325                 330

GAG ATC CTG TAC GGC TAC GAG TGG GAG CTG ACG AAG AGC CCT GCT GGC     1116
Glu Ile Leu Tyr Gly Tyr Glu Trp Glu Leu Thr Lys Ser Pro Ala Gly
    335                 340                 345

GCT TGG CAA TAC ACC GCC AAG GAC GGC GCC GGT GCC GGC ACC ATC CCG     1164
Ala Trp Gln Tyr Thr Ala Lys Asp Gly Ala Gly Ala Gly Thr Ile Pro
350                 355                 360                 365

GAC CCG TTC GGC GGG CCA GGG CGC TCC CCG ACG ATG CTG GCC ACT GAC     1212
Asp Pro Phe Gly Gly Pro Gly Arg Ser Pro Thr Met Leu Ala Thr Asp
                370                 375                 380

CTC TCG CTG CGG GTG GAT CCG ATC TAT GAG CGG ATC ACG CGT CGC TGG     1260
Leu Ser Leu Arg Val Asp Pro Ile Tyr Glu Arg Ile Thr Arg Arg Trp
            385                 390                 395

CTG GAA CAC CCC GAG GAA TTG GCC GAC GAG TTC GCC AAG GCC TGG TAC     1308
Leu Glu His Pro Glu Glu Leu Ala Asp Glu Phe Ala Lys Ala Trp Tyr
        400                 405                 410

AAG CTG ATC CAC CGA GAC ATG GGT CCC GTT GCG AGA TAC CTT GGG CCG     1356
Lys Leu Ile His Arg Asp Met Gly Pro Val Ala Arg Tyr Leu Gly Pro
    415                 420                 425

CTG GTC CCC AAG CAG ACC CTG CTG TGG CAG GAT CCG GTC CCT GCG GTC     1404
Leu Val Pro Lys Gln Thr Leu Leu Trp Gln Asp Pro Val Pro Ala Val
430                 435                 440                 445

AGC CAC GAC CTC GTC GGC GAA GCC GAG ATT GCC AGC CTT AAG AGC CAG     1452
Ser His Asp Leu Val Gly Glu Ala Glu Ile Ala Ser Leu Lys Ser Gln
                450                 455                 460

ATC CGG GCA TCG GGA TTG ACT GTC TCA CAG CTA GTT TCG ACC GCA TGG     1500
Ile Arg Ala Ser Gly Leu Thr Val Ser Gln Leu Val Ser Thr Ala Trp
            465                 470                 475

GCG GCG GCG TCG TCG TTC CGT GGT AGC GAC AAG CGC GGC GGC GCC AAC     1548
Ala Ala Ala Ser Ser Phe Arg Gly Ser Asp Lys Arg Gly Gly Ala Asn
        480                 485                 490

GGT GGT CGC ATC CGC CTG CAG CCA CAA GTC GGG TGG GAG GTC AAC GAC     1596
Gly Gly Arg Ile Arg Leu Gln Pro Gln Val Gly Trp Glu Val Asn Asp
    495                 500                 505

CCC GAC GGG GAT CTG CGC AAG GTC ATT CGC ACC CTG GAA GAG ATC CAG     1644
Pro Asp Gly Asp Leu Arg Lys Val Ile Arg Thr Leu Glu Glu Ile Gln
510                 515                 520                 525

GAG TCA TTC AAC TCC GCG GCG CCG GGG AAC ATC AAA GTG TCC TTC GCC     1692
Glu Ser Phe Asn Ser Ala Ala Pro Gly Asn Ile Lys Val Ser Phe Ala
                530                 535                 540
```

-continued

```
GAC CTC GTC GTG CTC GGT GGC TGT GCC GCC ATA GAG AAA GCA GCA AAG     1740
Asp Leu Val Val Leu Gly Gly Cys Ala Ala Ile Glu Lys Ala Ala Lys
            545                 550                 555

GCG GCT GGC CAC AAC ATC ACG GTG CCC TTC ACC CCG GGC CGC ACG GAT     1788
Ala Ala Gly His Asn Ile Thr Val Pro Phe Thr Pro Gly Arg Thr Asp
        560                 565                 570

GCG TCG CAG GAA CAA ACC GAC GTG GAA TCC TTT GCC GTG CTG GAG CCC     1836
Ala Ser Gln Glu Gln Thr Asp Val Glu Ser Phe Ala Val Leu Glu Pro
    575                 580                 585

AAG GCA GAT GGC TTC CGA AAC TAC CTC GGA AAG GGC AAC CCG TTG CCG     1884
Lys Ala Asp Gly Phe Arg Asn Tyr Leu Gly Lys Gly Asn Pro Leu Pro
590                 595                 600                 605

GCC GAG TAC ATG CTG CTC GAC AAG GCG AAC CTG CTT ACG CTC AGT GCC     1932
Ala Glu Tyr Met Leu Leu Asp Lys Ala Asn Leu Leu Thr Leu Ser Ala
                610                 615                 620

CCT GAG ATG ACG GTG CTG GTA GGT GGC CTG CGC GTC CTC GGC GCA AAC     1980
Pro Glu Met Thr Val Leu Val Gly Gly Leu Arg Val Leu Gly Ala Asn
            625                 630                 635

TAC AAG CGC TTA CCG CTG GGC GTG TTC ACC GAG GCC TCC GAG TCA CTG     2028
Tyr Lys Arg Leu Pro Leu Gly Val Phe Thr Glu Ala Ser Glu Ser Leu
        640                 645                 650

ACC AAC GAC TTC TTC GTG AAC CTG CTC GAC ATG GGT ATC ACC TGG GAG     2076
Thr Asn Asp Phe Phe Val Asn Leu Leu Asp Met Gly Ile Thr Trp Glu
    655                 660                 665

CCC TCG CCA GCA GAT GAC GGG ACC TAC CAG GGC AAG GAT GGC AGT GGC     2124
Pro Ser Pro Ala Asp Asp Gly Thr Tyr Gln Gly Lys Asp Gly Ser Gly
670                 675                 680                 685

AAG GTG AAG TGG ACC GGC AGC CGC GTG GAC CTG GTC TTC GGG TCC AAC     2172
Lys Val Lys Trp Thr Gly Ser Arg Val Asp Leu Val Phe Gly Ser Asn
                690                 695                 700

TCG GAG TTG CGG GCG CTT GTC GAG GTC TAT GGC GCC GAT GAC GCG CAG     2220
Ser Glu Leu Arg Ala Leu Val Glu Val Tyr Gly Ala Asp Asp Ala Gln
            705                 710                 715

CCG AAG TTC GTG CAG GAC TTC GTC GCT GCC TGG GAC AAG GTG ATG AAC     2268
Pro Lys Phe Val Gln Asp Phe Val Ala Ala Trp Asp Lys Val Met Asn
        720                 725                 730

CTC GAC AGG TTC GAC GTG CGC TGATTCGGGT TGATCGGCCC TGCCCGCCGA        2319
Leu Asp Arg Phe Asp Val Arg
    735                 740

TCAACCACAA CC                                                       2331
```

(2) INFORMATION FOR SEQ ID NO:21:

(i) SEQUENCE CHARACTERISTICS:
(A) LENGTH: 740 amino acids
(B) TYPE: amino acid
(D) TOPOLOGY: linear (ii) MOLECULE TYPE: protein (xi) SEQUENCE DESCRIPTION: SEQ ID NO:21:

```
Val Pro Glu Gln His Pro Pro Ile Thr Glu Thr Thr Thr Gly Ala Ala
  1               5                  10                  15

Ser Asn Gly Cys Pro Val Val Gly His Met Lys Tyr Pro Val Glu Gly
             20                  25                  30

Gly Gly Asn Gln Asp Trp Trp Pro Asn Arg Leu Asn Leu Lys Val Leu
        35                  40                  45

His Gln Asn Pro Ala Val Ala Asp Pro Met Gly Ala Ala Phe Asp Tyr
     50                  55                  60

Ala Ala Glu Val Ala Thr Ile Asp Val Asp Ala Leu Thr Arg Asp Ile
```

-continued

```
 65                  70                  75                  80

Glu Glu Val Met Thr Thr Ser Gln Pro Trp Trp Pro Ala Asp Tyr Gly
                 85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Gly Met Gln Arg
        115                 120                 125

Phe Ala Pro Leu Asn Ser Trp Pro Asp Asn Ala Ser Leu Asp Lys Ala
    130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270

Gly Lys Thr His Gly Ala Gly Pro Ala Asp Leu Val Gly Pro Glu Pro
        275                 280                 285

Glu Ala Ala Pro Leu Glu Gln Met Gly Leu Gly Trp Lys Ser Ser Tyr
    290                 295                 300

Gly Thr Gly Thr Gly Lys Asp Ala Ile Thr Ser Gly Ile Glu Val Val
305                 310                 315                 320

Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365

Gly Gly Pro Gly Arg Ser Pro Thr Met Leu Ala Thr Asp Leu Ser Leu
    370                 375                 380

Arg Val Asp Pro Ile Tyr Glu Arg Ile Thr Arg Arg Trp Leu Glu His
385                 390                 395                 400

Pro Glu Glu Leu Ala Asp Glu Phe Ala Lys Ala Trp Tyr Lys Leu Ile
                405                 410                 415

His Arg Asp Met Gly Pro Val Ala Arg Tyr Leu Gly Pro Leu Val Pro
            420                 425                 430

Lys Gln Thr Leu Leu Trp Gln Asp Pro Val Pro Ala Val Ser His Asp
        435                 440                 445

Leu Val Gly Glu Ala Glu Ile Ala Ser Leu Lys Ser Gln Ile Arg Ala
    450                 455                 460

Ser Gly Leu Thr Val Ser Gln Leu Val Ser Thr Ala Trp Ala Ala Ala
465                 470                 475                 480

Ser Ser Phe Arg Gly Ser Asp Lys Arg Gly Gly Ala Asn Gly Gly Arg
                485                 490                 495
```

-continued

```
Ile Arg Leu Gln Pro Gln Val Gly Trp Glu Val Asn Asp Pro Asp Gly
            500                 505                 510

Asp Leu Arg Lys Val Ile Arg Thr Leu Glu Glu Ile Gln Glu Ser Phe
        515                 520                 525

Asn Ser Ala Ala Pro Gly Asn Ile Lys Val Ser Phe Ala Asp Leu Val
    530                 535                 540

Val Leu Gly Gly Cys Ala Ala Ile Glu Lys Ala Ala Lys Ala Ala Gly
545                 550                 555                 560

His Asn Ile Thr Val Pro Phe Thr Pro Gly Arg Thr Asp Ala Ser Gln
                565                 570                 575

Glu Gln Thr Asp Val Glu Ser Phe Ala Val Leu Glu Pro Lys Ala Asp
            580                 585                 590

Gly Phe Arg Asn Tyr Leu Gly Lys Gly Asn Pro Leu Pro Ala Glu Tyr
        595                 600                 605

Met Leu Leu Asp Lys Ala Asn Leu Leu Thr Leu Ser Ala Pro Glu Met
    610                 615                 620

Thr Val Leu Val Gly Gly Leu Arg Val Leu Gly Ala Asn Tyr Lys Arg
625                 630                 635                 640

Leu Pro Leu Gly Val Phe Thr Glu Ala Ser Glu Ser Leu Thr Asn Asp
                645                 650                 655

Phe Phe Val Asn Leu Leu Asp Met Gly Ile Thr Trp Glu Pro Ser Pro
            660                 665                 670

Ala Asp Asp Gly Thr Tyr Gln Gly Lys Asp Gly Ser Gly Lys Val Lys
        675                 680                 685

Trp Thr Gly Ser Arg Val Asp Leu Val Phe Gly Ser Asn Ser Glu Leu
    690                 695                 700

Arg Ala Leu Val Glu Val Tyr Gly Ala Asp Asp Ala Gln Pro Lys Phe
705                 710                 715                 720

Val Gln Asp Phe Val Ala Ala Trp Asp Lys Val Met Asn Leu Asp Arg
                725                 730                 735

Phe Asp Val Arg
            740

(2) INFORMATION FOR SEQ ID NO:22:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:22:

GACGCNNNNN NNNNN                                                     15
```

MUTATIONS IN THE KATG GENE USEFUL FOR DETECTION OF *M. TUBERCULOSIS*

This is a continuation-in-part application U.S. patent application Ser. No. 08/418,782, filed Apr. 7, 1995, now U.S. Pat. No. 5,658,733, issued Aug. 19, 1997 which is a continuation-in-part of U.S. patent application Ser. No. 08/228,662, filed Apr. 18, 1994, now U.S. Pat. No. 5,688, 639, issued Nov. 18, 1997 both of which are incorporated herein by reference.

BACKGROUND OF THE INVENTION

Despite more than a century of research since the discovery of *Mycobacterium tuberculosis*, the aetiological agent of tuberculosis, this disease remains one of the major causes of human morbidity and mortality. There are an estimated 3 million deaths annually attributable to tuberculosis (sec, D. Snider, *Rev. Inf. Dis.*, S335 (1989)), and although the majority of these are in developing countries, the disease is assuming renewed importance in the W. due to the increasing number of homeless people and the impact the AIDS epidemic (see, R. E. Chaisson et al., *Am. Res. Resp. Dis.*, 23, 56 (1987); D. E. Snider, Jr. et al., *New Engl. J. Med,* 326, 703 (1992); M. A. Fischl et al., *Ann. Int. Med.,* 117, 177 (1992) and ibid. at 184.

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (G. Middlebrook, *Am. Rev. Tuberc.,* 69, 471(1952) and J. Youatt, *Am. Rev. Resp. Dis.,* 99, 729 (1969)). Neither the precise target of the drug, nor its made of action are known, but INH treatment results in the perturbation of several metabolic pathways of the bacterium. However, shortly after its introduction, INH-resistant isolates of *Mycobacterium tuberculosis* emerged. See M. L. Pearson et al., *Ann. Int. Med.,* 117, 191(1992) and S. W. Dooley et al., *Ann. Int. Med.,* 117, 257 (1992).

Several investigators have associated the toxicity of INH for mycobacteria with endogenous catalase activity. See, for example, "Isonicotinic acid hydrazide," in F. E. Hahn, *Mechanism of Action of Antibacterial Agents*, Springer-Verlag (1979) at pages 98–119. This relationship was strengthened by a recent report by Ying Zhang and colleagues in *Nature,* 358, 591 (1992) which described the restoration of INH susceptibility in an INH resistant *Mycobacterium smegmatis* strain after transformation using the catalase-peroxide (katG) gene from an INH sensitive *M. tuberculosis* strain. In a follow-up study, Zhang and colleagues in *Molec. Microbiol.,* 8, 521 (1993) demonstrated the restoration of INH susceptibility in INH resistant *M. tuberculosis* strains after transformation by the functional katG gene. As reported by B. Heym et al., *J. Bacieriol.,* 175, 4255 (1993), the katG gene encodes for a 80,000-dalton protein.

A conclusive diagnosis of tuberculosis depends on the isolation and identification of the etiologic agent, *Mycobacterium tuberculosis*, which generally requires 3–8 weeks. Design of an appropriate therapeutic regimen depends on the results of subsequent antituberculosis susceptibility testing by the agar dilution method and produces additional delays of 3–6 weeks (Roberts et al., "Mycobacerium" in *Manual of Clincial Microbiology,* 5th Ed.; A. Balows et al., Eds.; American Society for Microbiology: Washington; pp. 304–399 (1991). Identifcaiton and drug resistance testing can now also be accomplished more quickly by using the BACTEC radiometric method. (Tenover et al., *J. Clin. Microbiol.,* 31 767–779 (1993) and Huebner et al., *J. Clin. Microbiol.,* 31, 771–775 (1993). Acid fast bacilli are detected in the BACTEC bottle, and and identification is made using a nucleic acid hybridization technique on the BACTEC-derived growth. Drug susceptibility testing is then conducted using the same BACTEC growth to inoculate fresh BACTEC bottles containing various antituberculosis drugs. This procedure reduces the time needed to generate a complete analysis, but the total time required to report susceptibility results for MTB is typically in excess of 20 days. The need to minimize the transmission of newly identified drug resistant strains of MTB requires the development of much more rapid identification procedures.

The rapid detection of *M. tuberculosis* directly from clinical samples has been possible recently by virtue of the availability of polymerase chain reaction (PCR) and the recognition of diagnostic sequences amplified by the appropriate primers. The ability to conduct PCR analyses depends on having a high enough gene or gene product concentration so that the molecular tools work efficiently even when the organism numbers are low. Thus, the most efficient molecular assays used to detect *M. tuberculosis* depend on the IS6110 insertion sequence (about 10 copies) or the 16S ribosomal RNA (thousands of copies). See, respectively, K. D. Eisenach et al., *J. Infect. Dis.,* 61, 997 (1990) and N. Miller et al., *Abstracts ASM*, Atlanta, Ga. (1993) at page 177. However, these methods do not provide any information regarding the drug-resistance phenotype of the *M. tuberculosis* strain.

Recently, B. Heym et al. (PCT WO 93122454) disclose the use of polymerase chain reaction to amplify portions of the katG gene of putative resistant strains. The PCR products were evaluated by single-strand conformation polymorphism (SSCP) analysis, wherein abnormal strand motility on a gel is associated with mutational events in the gene. For example, in five strains, a single base difference was found in a 200 bp sequence, a G to T transversion at position 3360. This difference would result in the substitution of Arg-461 by Leu. However, carrying out SSCP on a given clinical sample can be a laborious procedure that requires sequencing to confirm whether mutations or deletions predictive of drug resistance are in fact present in the target gene.

There is a continuing need in the art to develop a simple test permitting the rapid identification of *M. tuberculosis* and its drug-resistance phenotype.

SUMMARY OF THE INVENTION

The present invention provides a method to rapidly identify strains of *M. tuberculosis* which are resistant to isoniazid (INH). The method is based on our discovery that certain mutations in the katG gene of *M. tuberculosis* which confer INH resistance coincidentally result in the addition or deletion of restriction sites, which are recognized by various restriction enzymes. For example, the wild-type (WT) katG gene of *M. tuberculosis* contains an NciI-MspI restriction site spanning codon 463, which site is absent in the corresponding codon 463 in a number of INH resistant strains due to a single base mutation in that codon. An NciI-MspI) restriction site is a site cleaved by both NciI and MspI. This site is represented by the nucleotide sequence CCGGG (see Table 1).

Alternatively, or in addition, some INH resistant strains have a single base mutation in codon 315 in the katG gene that produces a new MspI restriction site associated with the corresponding codon 315 in the INH resistant strain. Some INH resistant strains have a single base mutation at codon 337 that results in the deletion of a RsaI restriction site otherwise present at the corresponding position in the WT gene; and some have a single base mutation at codon 264 that eliminates a CfoI restriction site. These mutations may be present singly or in combination in INH resistant *M. tuberculosis* strains.

When used in reference to nucleotide position, codon position or restriction site position, the term "corresponding" is defined to mean the same absolute location on two different *M. tuberculosis* katG genes, wherein absolute location is defined by the numbering system used in FIG. 7 (SEQ ID NO:20). For example, a wild-type codon 463 represented by CGG at nucleotide positions 1456–1458 on a wild-type katG gene of *M. tuberculosis* and a mutant codon 463 represented by CTG at the same nucleotide positions 1456–1458 on a katG gene of an INH resistant strain of *M. tuberculosis* are considered to be corresponding codons.

The determination of whether one or more of these identifying mutations in the katG gene are present in a strain of *M. tuberculosis* can be made by employing the techniques of restriction fragment length polymorphism (RFLP) analysis. Therefore, in an embodiment directed to the identification of a mutation in codon 463 that is associated with INH resistance, the present assay comprises the steps of:

(a) amplifying a portion of the katG gene of an *M. tuberculosis* isolate to yield a detectable amount of DNA comprising the nucleotide position occupied by base 1457 of the *M. tuberculosis* katG gene consensus sequence depicted in FIG. 7 (SEQ ID NO:20); and (b) determining whether an NciI-MspI restriction site is absent in codon 463 of said katG gene, wherein said absence is indicative of an INH resistant strain of *M. tuberculosis.*

The RFLP technique involves cleaving the DNA with a restriction endonuclease which cleaves at an NciI-MspI restriction site to yield at least one DNA fragment and determining whether the number and location of the fragments is indicative of the absence of an NciI-MspI restriction site in codon 463 of said katG gene, wherein said absence is indicative of an INH resistant strain of *M. tuberculosis*, preferably by employing the techniques of gel electrophoresis.

If the amplified DNA of step (a) contains no NciI-MspI restriction sites, then the DNA fragment yielded in step (b) will be identical to the amplified DNA of step (a). This can occur where the portion of the katG gene amplified in step (a) is from an INH resistant strain of *M. tuberculosis* having a mutation in codon 463 that removes the NciI-MspI restriction site spanning that codon in the wild-type katG gene, and having no other additional NciI-MspI restriction sites.

In order for the amplified DNA to yield a meaningful RFLP pattern, the portion of the katG gene amplified in step (a) will be of sufficient length to produce fragments of sufficient length to visualize using gel electrophoresis. In the above-described embodiment, for example, the portion amplified will contain a sufficient number of bases to either side (5' or 3') of codon 463 such that cleavage at a site spanning that codon will yield fragments that can be visualized using gel electrophoresis.

In another embodiment of the invention directed to the additional identification of a mutation in codon 315 associated with INH resistance, the amplified DNA of step (a) further comprises at least one MspI restriction site and the nucleotide position occupied by base 1013 (FIG. 7, SEQ ID NO:20), and the determination made in step (b) further includes whether an MspI restriction site associated with codon 315 is present, wherein said presence is indicative of an INH resistant strain. For example, RFLP can also be employed to determine whether the number and location of the fragments is indicative of the codon 315 MspI restriction site. Preferably, the portion of the katG locus which is amplified is a minor portion of the entire katG gene, i.e., less than 1500 base pair, more preferably less than 1000 base pair, and is isolated and amplified by polymerase chain reaction, as described hereinbelow. The term "location" refers to the Rf (relative electrophoretic mobility) of a given fragment on the gel.

The pattern of fragments produced on a gel by electrophoresis of a restriction digest of an amplified portion of the katG gene of an *M. tuberculosis* strain of interest, such as an INH resistant strain, is preferably compared to the pattern produced in a digest of an equivalent portion of the katG gene of a wild-type (WT) control strain of *M. tuberculosis*, which strain is INH sensitive. The term "equivalent" is defined herein to mean that any two portions of the katG gene would comprise the same number and location of restriction sites being analyzed (e.g., sites recognized by CfoI, RsaI, MspI, and/or NciI) if the portions both were selected from a portion of the DNA of SEQ ID NO:20 (i.e., if there were no mutations altering the number of restriction sites of the type being analyzed), and that the portions do not differ in size before cleavage to the extent that the number of fragments obtained cannot be compared following side-by-side gel electrophoresis and visualization of the resultant fragments, as described hereinbelow. For example, the control katG DNA can correspond to an equivalent portion of SEQ ID NO:20 (FIG. 7, upper sequence) comprising one or more of the codons of interest (e.g., codons 315 or 463) and their associated restriction sites. As discussed below, such a portion of DNA can be derived from strain H37Rv MC. A positive control corresponding to DNA fragments derived from a known INH resistant strain may also be used.

In the embodiment of the assay of the invention directed to the determination of the presence or absence of a NciI-MspI restriction site associated with codon 463, gel electrophoresis is employed to compare the number and location of the DNA fragments to the number and location of DNA fragments derived from cleavage of DNA derived from an equivalent portion of the katG gene wherein the NciI-MspI restriction site at codon 463 is present, wherein a determination of the absence of the restriction site at codon 463 in the katG gene is indicative of an INH resistant strain of *M. tuberculosis.* Preferably, the control DNA sequence of the portion of the katG gene wherein the codon 463 restriction site is present corresponds to a portion of SEQ ID NO:20 (FIG. 7, upper sequence). For example, the control DNA may contain five NciI-MspI restriction sites in each DNA molecule prior to cleavage, and the DNA of step (a), which is derived from an INH resistant strain, may contain four NciI-MspI restriction sites in each DNA molecule prior to cleavage. The assay also preferably includes positive control DNA fragments derived from an INH resistant strain which does not include the codon 463 NciI-MspI restriction site in the katG gene.

The present invention also provides method for selectively detecting *M. tuberculosis* in a DNA sample, wherein the DNA is amplified to generate a detectable amount of amplified DNA comprising a katG DNA fragment which consists of base 904 through base 1523 of the *M. tuberculosis* katG gene. The generation of this katG DNA fragment is indicative of the presence of *M. tuberculosis* in the sample. Preferably, the DNA sample is a human biological tissue or fluid, more preferably a human biological fluid. The DNA sample is most preferably human sputum. Advantageously, the method of the invention can be performed on clinical human sputum samples with minimal pretreatment of the clinical sample.

In a preferred embodiment of the *M. tuberculosis* detection method, the katG DNA fragment has a restriction site that comprises either a G or a C at the nucleotide position occupied by base 1013 in codon 315 of the *M. tuberculosis* katG gene as depicted in FIG. 7 (SEQ ID NO:20), and the method further comprises contacting the katG DNA fragment with a restriction endonuclease, preferably MspI, that cleaves either at the restriction site comprising a G at the nucleotide position occupied by base 1013 of codon 315, or at the restriction site comprising a C at the nucleotide position occupied by base 1013 of codon 315, but not both, yielding at least one cleaved fragment. The at least one cleaved fragment is electrophoresed to yield an electrophoretic mobility pattern comprising the at least one cleaved fragment, and the mobility pattern is analyzed to selectively detect the presence of *M. tuberculosis* in the sample. Preferably, restriction fragment length polymorphism (RFLP) analysis is used to analyze the electrophoretic mobility pattern generated by gel electrophoresis of the cleaved fragments to detect *M. tuberculosis.*

In another embodiment of the *M. tuberculosis* detection method, *M tuberculosis* is selectively detected in a DNA sample by:

(a) amplifying the DNA to generate a detectable amount of amplified DNA comprising a katG DNA fragment comprising base 904 through base 1523 of the *M. tuberculosis* katG gene, wherein the katG DNA fragment further comprises a restriction site comprising either a G or a C at the nucleotide position occupied by base 1013 in codon 315 of the *M. tuberculosis* katG gene as depicted in FIG. 7 (SEQ ID NO:20);

(b) contacting the katG DNA fragment with a restriction endonuclease, preferably MspI, that cleaves either at said restriction site comprising a G at the nucleotide position occupied by base 1013 of codon 315, or at said restriction site comprising a C at the nucleotide position occupied by base 1013 of codon 315, but not at both of said restriction sites, to yield at least one cleaved fragment;

(c) electrophoresing, preferably using gel electrophoresis, the at least one cleaved fragment to yield an electrophoretic mobility pattern comprising the at least one cleaved fragment; and (d) analyzing the mobility pattern, preferably using RFLP, to selectively detect the presence of *M. tuberculosis* in the sample.

In a further embodiment of the *M. tuberculosis* detection method, *M. tuberculosis* is selectively detected a sample containing DNA by:

(a) amplifying the DNA to generate a detectable amount of amplified DNA comprising a katG DNA fragment comprising base 904 through base 1523 of the *M. tuberculosis* katG gene as depicted in FIG. 7 (SEQ ID NO:20);

(b) contacting the katG DNA fragment with a restriction endonuclease, preferably MspI, that cleaves at C/CGG to yield at least one cleaved fragment;

(c) electrophoresing, preferably using gel electrophoresis, the at least one cleaved fragment to yield a mobility pattern comprising the at least one cleaved fragment; and (d) analyzing the mobility pattern, preferably using RFLP, to selectively detect the presence of *M. tuberculosis* in the sample.

In a particularly preferred embodiment, the *M. tuberculosis* detection method further comprises determining whether or not the katG DNA fragment has a S315T mutation, preferably using a restriction digest followed by gel electrophoresis of the digested DNA and RFLP analysis of the electrophoretic mobility patterns, wherein the presence of a S315T mutation is indicative of an INH-resistant strain of *M. tuberculosis.*

The present invention also provides oligonucleotides and subunits thereof useful in pairs as primers to initiate the polymerase chain reaction (PCR). Subunits of at least seven bases in length are preferred. PCR is useful both to amplify katG DNA so as to prepare both the target DNA of step (a) of the present process, as well as the DNA which is used to prepare the control digest.

The present invention also provides isolated, purified DNA represented by the consensus sequence derived for the *M. tuberculosis* katG gene. This DNA was found to occur in nature as the katG gene of *M. tuberculosis* strain H37Rv MC, as maintained at the Mayo Clinic, and is also referred to as the wild-type (WT) DNA. The present invention also includes isolated, purified DNA encoding the consensus amino acid sequence encoded by the consensus wild-type katG DNA, as well as DNA sequences that differ in sequence but which also encode this amino acid sequence (a consensus catalase peroxidase polypeptidc) and can be employed to provide the isolated, purified polypeptide represented by the consensus amino acid sequence, which polypeptide is also provided by the invention.

The polypeptide of the invention can be prepared by expression in transformed host cells, such as bacteria, yeast, plant, or insect cells transformed with the DNA sequences of the present invention, operatively linked to regulatory regions functional in the transformed host cells. The polypeptide can be used as a standard *M. tuberculosis* catalase peroxidase, to correlate enzymatic activity (relative level, loss and restoration), with INH modification and degradation and drug resistance in *M. tuberculosis.*

The present invention also provides a kit comprising, separately packaged in association:

(a) a pair of oligonucleotide primers selected so as to amplify a portion of the DNA of the *M. tuberculosis* katG gene comprising base 1457 in codon 463 or base 1013 in codon 315, as depicted in FIG. 7 (SEQ ID NO:20); and (b) an amount of a restriction endonuclease such as MspI, effective to cleave the amplified portion of said DNA at a restriction site comprising said base 1457 or said base 1013.

The present kits will also preferably comprise instruction means for carrying out the present assay, i.e., a printed package insert, tag or label, or an audio or video tape. The present kits will also preferably comprise a control DNA digest prepared by amplifying a portion of the consensus DNA of SEQ ID NO:20 (FIG. 7), that is equivalent to the portion defined and amplified by the pair of primers, followed by digestion of the DNA with a suitable restriction endonuclease such as MspI.

The present invention is exemplified by the use of NciI, MspI, CfoI, and RsaI digestions, with the use of MspI digestion being preferred; however, any restriction endonuclease having a restriction site spanning all or a portion of codon 463, codon 315, codon 337, or codon 264, which portion contains the site of the single base mutation associated with INH resistance as identified in Table 2, may be used, as desired. For example, the restriction endonucleases listed in Table 1 can be employed. Particularly preferred are restriction endonucleases having a restriction site that contains the position occupied by base 1457 in codon 463, or base 1013 in codon 315, as depicted in FIG. 7 (SEQ ID NO:20).

TABLE 1

| *M. tuberculosis** katG gene Specificity | Restriction Site | Restriction Enzyme |
|---|---|---|
| Cuts 264-A (sensitive) | C/CGC | AciI[a] |
| | GC/NGC[b] | BsoFI, Fnu4HI, Bsp6I, BssFI, BssXI, Cac824I, CcoP215I, CcoP216I, FbrI, ItaI, Uur960I |
| | R/GCGCY[c] | Bsp143II, HaeII, Bme14ZI, BsmHI, Bst1473II, Bst16I, Btu34II, HinHI, LpnI, NgoI |
| | G/CGC | CfoI, HhaI, BcaI, CcoP95I, Csp1470I, FnuDIII, Hin6I, Hin7I, HinGUI, HinPII, IlinSII, IlinS2I, MnnIV, SciNI |
| Cuts 264-T (resistant) | GACGCNNNNN/NNNNN (SEQ ID NO:22) | HgaI |
| Cuts 337-Y (resistant) | GT/AC | RsaI, AfaI, Asp16HI, Asp17HI, Asp18HI, Asp29HI, CcoP73I, Csp6I, CviQI, CviRII |
| Cuts 337-C (resistant) | GC/NGC | BsoFI, Fnu1HI, Bsp61, BssFI, BssFI, BssXI, Cac824I, CcoP215I, CcoP216I, FbrI, ItaI, Uur960I |
| | C/CGC | AciI[a] |
| Cuts 315-S (sensitive) | C/CGC | AciI[a] |
| | GC/NGC | BsoFI, Fnu4HI, Bsp6I, BssFI, BssXI, Cac824I, CcoP215I, CcoP216I, FbrI, ItaI, Uur960I |
| | CMG/CKG[d] | MspAII, NspBII |
| Cuts 315-T (resistant) | R/CCGGY[e] | BsrFI, Cfr10I, Bco118I, Bse118I, Bsp21I, BssAI |
| | C/CGG | MspI, Bsu1192I, BsuFI, FinII, HapII, Hin2I, Hin5I, HpaII, MniII, MnoI, MspI, Pde137I, Pme35I, SecII, SfaGUI, Sth134I, Uba1128I, Uba1141I, Uba1267I, Uba1338I, Uba1355I, Uba1439I |
| Cuts 463-R (sensitive) | CC/SGG[f] | NciI, BcnI, AhaI |
| | C/CGG | MspI, Bsu1192I, BsuFI, FinII, HapII, Hin2I, Hin5I, HpaII, MniII, MnoI, MspI, Pde137I, Pme35I, SecII, SfaGUI, Sth134I, Uba1128I, Uba1141I, Uba1267I, Uba1338I, Uba1355I, Uba1439I |
| Cuts 463-L (resistant) | CAG/NNN/CTG | AlwNI |
| | CC/WGG[g] | BstNI, BstOI, MvaI |
| | /CCWGG | EcoRII |

[a]AciI cleaves the complementary strand of the katG gene;
[b]N = C or G or A or T;
[c]R = A or G;
[d]M = A or C, K = G or T;
[e]Y = C or T;
[f]S = C or G;
[g]W = A or T.

TABLE 2[a]

| | | | | |
|---|---|---|---|---|
| 264-A (sensitive)[b] | (SEQ ID NO:8) | 847 | GTC GAA ACA GCG GCG CTG ATC GTC GGC | 873 |
| 264-T (resistant) | (SEQ ID NO:9) | | GTC GAA ACA GCG ACG CTG ATC GTC GGC | |
| 337-Y (sensitive)[c] | (SEQ ID NO:10) | 1066 | CTC GAG ATC CTG TAC GGC TAC GAG TGG | 1092 |
| 337-C (resistant) | (SEQ ID NO:11) | | CTC GAG ATC CTG TGC GGC TAC GAG TGG | |
| 315-S (sensitive)[d] | (SEQ ID NO:12) | 1000 | GAC GCG ATC ACC AGC GGC ATC GAG GTC | 1026 |
| 315-T (resistant) | (SEQ ID NO:13) | | GAC GCG ATC ACC ACC GGC ATC GAG GTC | |
| 463-R (sensitive)[e] | (SEQ ID NO:14) | 1444 | AAG AGC CAG ATC CGG GCA TCG GGA TTG | 1470 |

TABLE 2[a]-continued

| | | |
|---|---|---|
| 463-L (resistant) | (SEQ ID NO:15) | AAG AGC CAG ATC CTG GCA TCG GGA TTG |

[a]The underlined codons represent the sites where the indicated single base mutations confer INH resistance. The bold bases indicate restriction sites as follows: G/CGC for CfoI in 264-A (sensitive); GT/AC for RsaI in 337-Y (sensitive); C/CGG for MspI in 315-T (resistant) and 463-R (sensitive). For ease of reference, the partial sequences shown in this table include the 12 bases to either side of the affected codon;the numbering system is the same as used for the wild-type consensus sequence in FIGS. 1 and 7. The full sequence of bases to either side of the affected codon is shown in FIG. 7. In each of the sensitive/resistant pairs shown in this table, the upper sequence is the consensus, wild-type sequence (INR-sensitive) and the lower sequence is the mutant (INH-resistant) sequence.
[b]codon 264
GCG = ala (A)
ACG = thr (T)
[c]codon 337
TAC = tyr (Y)
TGC = cys (C)
[d]codon 315
AGC = ser (S)
ACC = thr (T)
[e]codon 463
CGG = arg (R)
CTG = leu (L)

BRIEF DESCRIPTION OF THE DRAWINGS

FIG. 1, panels A–D, depicts the consensus, wild-type DNA sequence of the *M. tuberculosis* katG gene as the upper of the pair of sequences (61–2295) (SEQ ID NO:1). This DNA sequence data has been submitted to Gen Bank and has been assigned accession number UO6262. The lower of the pair of sequences depicts nucleotide sequence 1970–4190 of the KpnI fragment bearing the katG gene as depicted in FIG. 6 of Institute Pasteur et al. (published PCT application WO 93/22454). This sequence (SEQ ID NO:2) has been deposited in the EMBL data library under accession number X68081 (Gen Bank X68081. gb_ba). Dots (.) above the sequence mark every tenth base. The upper sequence is in lower case in areas where variation in the sequence among isolates described hereinbelow and the consensus sequence was found. The arrow before position 70 and after position 2291 of the upper sequence indicate the coding sequence of the katG gene.

FIG. 2 depicts the katG amino acid consensus sequence derived from 15 strains of *M. tuberculosis* (SEQ ID NO:7).

FIG. 7, panels A–C, depict as the upper of the pair of sequences the consensus, wild-type DNA sequence of the *M. tuberculosis* katG gene (SEQ ID NO:20), and as the lower of the pair of sequences the amino acid consensus sequence encoded thereby (SEQ ID NO:21). This information is updated from that presented in FIGS. 1 (SEQ ID NO:1) and 2 (SEQ ID NO:7) and the numbering system is as used therein. The amino acid and nucleotide sequences are arranged in this figure so as to facilitate convenient determination of which codons encode which amino acid in the polypeptide sequence.

DETAILED DESCRIPTION OF THE INVENTION

Figure 3:
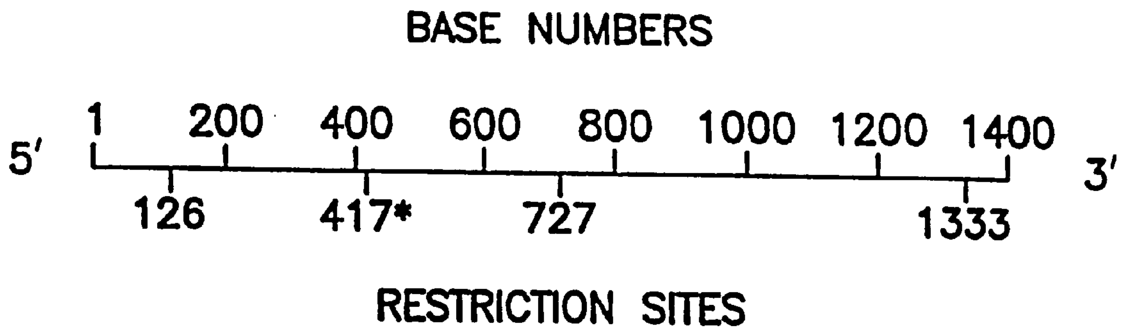
FIG. 3 schematically depicts the NciI restriction sites for the part B amplicon of katG. The (*) depicts the site of the Arg→Leu mutation which is found in some INH resistant *M. tuberculosis* strains.

Wild type strains of *M. tuberculosis* are highly susceptible to isoniazid (INH) with minimum inhibitory INH concentration (MIC or $IC_{min}$)≦0.02 μg/ml, and a susceptible strain is considered to be one with an $IC_{min}$<1.0 μg/ml. At the Mayo Clinic, Rochester, Minn., clinical strains of *M. tuberculosis* (including MDR-TB strains) were identified which exhibit intermediate to high level resistance to INH ($IC_{min}$ range 1.0 to>32 μg/ml). Many of these strains, especially those highly resistant to INH (≧4.0 μg/ml), exhibited diminished catalase activity as assessed by a semiquantitative technique. The mean semiquantitative catalase was 16.5 mm for 6/15 strains with INH $IC_{min}$<1.0 μg/ml and 13.3 mm for 9/15 strains with $IC_{min}$≧1.0 μg/ml.

To develop the present assay, it was first necessary to determine whether some *M. tuberculosis* strains have decreased INH sensitivity as a result of katG gene mutations. Therefore, the nucleic acid sequences of the katG genes for both INH sensitive ($IC_{min}$<1.0 μg/ml) and INH resistant ($IC_{min}$≧1.0 μg/ml) *M. tuberculosis* strains were determined. From the DNA sequencing data generated, a katG consensus sequence was derived, and katG sequences from all 15 *M. tuberculosis* strains (INH sensitive and INH resistant) were compared to the consensus sequence to determine katG deviations.

Five of nine INH resistant strains (INH $IC_{min} \geqq 1.0$ μg/ml) had one or more missense mutations; one had a nonsense mutation; one had an 8 base pair deletion; and two had no mutations in the coding sequences. All of the five strains with missense mutations had a common G to T transversion at base 1457 in codon 463 (bases 1456–1458) causing replacement of arginine with leucine and loss of an NciI-MspI restriction site. Two of those having mutations at codon 463 also showed a G to C transversion at base 1013 in codon 315 (bases 1012–1014) causing replacement of serine with threonine. A third contained a G to A transversion at base 859 in codon 264 (bases 859–861) resulting in the replacement of alanine by threonine, and a fourth contained an A to G transversion at base 1079 in codon 337 (bases 1078–1080), causing tyrosine to be replaced by cysteine. The numbering system is shown in FIG. 1 (SEQ ID NO:1). The affected codons and portions of the DNA sequences on either side are shown for both INH sensitive and INH resistant strains in Table 2.

Six INH sensitive strains (INH $IC_{min} < 1.0$ μg/ml) were also sequenced and found to have from none to 5 amino acid differences with the consensus sequence of all 15 strains, but none of the mutations affected codons 463, 315, 264, or 337 or their overlapping restriction sites. Restriction analysis of a total of 32 sensitive and 43 resistant strains revealed a common restriction fragment length polymorphism (RFLP) in nearly half (19) of the 43 of INH resistant strains, but only one of the INH sensitive strains. Specifically, 44% of the INH resistant had lost the NciI-MspI restriction site at the locus of codon 463 while only 1 of 32 sensitive strains had this restriction polymorphism.

Subsequently, the frequency of codon 463 (R→L) and codon 315 (S→T) mutations in 97 *M. tuberculosis* clinical isolates was determined. These isolates were obtained from patients treated at Mayo Clinic and samples referred from other health care institutions. Restriction fragment length polymorphism (RFLP) analysis using the MspI restriction enzyme, which cleaves at a site spanning the consensus codon 463 site and at a site comprising a portion of the mutant codon 315 site on the katG gene of *M. tuberculosis*, was performed on amplified DNA from 97 clinical isolates. Comparison of the resulting RFLP patterns and $IC_{min}$ for isoniazid revealed that of the 90 INH-resistant strains, approximately 10% had both mutations, 20% had the 315 S→T mutation only, and 26% had the 463 R→L mutation only. Thus, 51 of the 90 resistant strains were identified by RFLP as having mutations at codons 463, 315 or both, resulting in a detection of over 50% of the resistant strains by this molecular method in a single experiment. Only one of the seven INH sensitive strains was found to have the 463 R→L mutation, and none of the INH sensitive strains had the 315 S→T mutation. Greater INH resistance (>4.0 μg, INH/ml) is associated with the 315 S→T mutation, but not if the 463 R→L mutation is also present.

These results indicate that two mutations, arginine→leucinc in codon 463 and serine→threonine in codon 315 of the *M. tuberculosis* catalase-peroxidase (katG) gene occur in a significant fraction of INH resistant *M. tuberculosis* strains (INH $IC_{min} > 1.0$ μg/ml). Furthermore, these single base mutations can be determined using a rapid relatively simple method, i.e., PCR amplification, digestion and monitoring for a loss of an NciI and/or an MspI restriction site at codon 463, and the addition of an MspI restriction site at codon 315, by RFLP, as described in detail hereinbelow. Other restriction endonucleases can be used to determine whether or not these single base mutations exist in a katG gene of interest, as long as the restriction site cleaved by the restriction endonucleases contains the affected base, such that the endonuclease cleaves the wild-type sequence but not the corresponding mutant sequence, or vice versa. Although in a preferred embodiment of the invention, the number and location of the fragments is determined by gel electrophoresis, the presence or absence in the digest of a fragment comprising the indicated restriction sites can be determined by other methods known to the art, including immunoassays (dot blots and reverse dot blots), DNA probes, microtiter well capture and the like.

Figure 5:
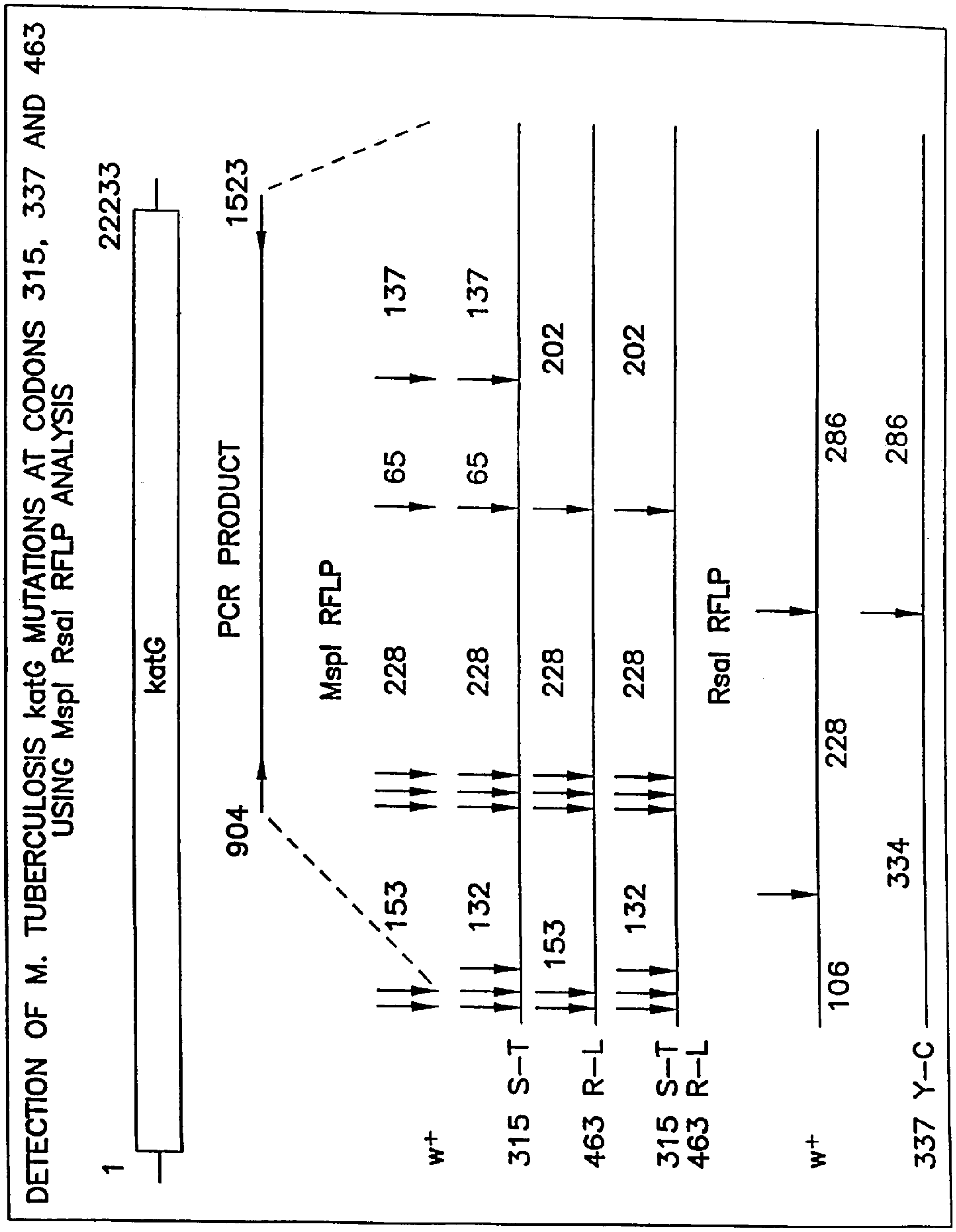
FIG. 5 schematically depicts MspI and RsaI restriction sites and resulting RFLP fragments for a portion of the *M. tuberculosis* katG gene. For MspI, restriction maps for wild-type (W+), single (315 Ser→Thr or 463 Arg→Leu) mutants and the double (315 Ser→Thr and 463 Arg→Leu) mutant are shown. For RsaI, restriction maps for wild-type (W+) and the 337 W→C mutant are shown.
Figure 6:
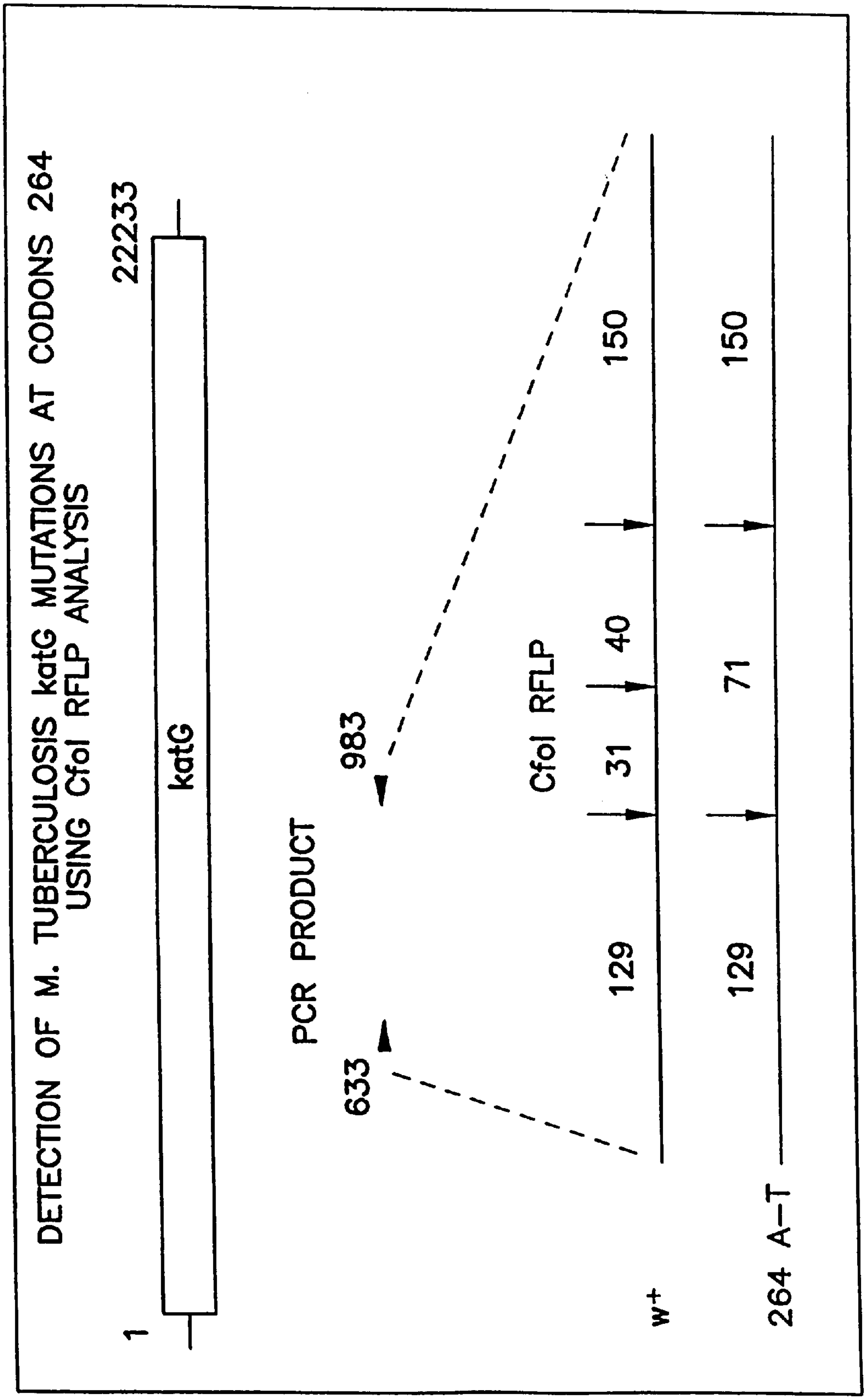
FIG. 6 schematically depicts CfoI restriction sites and resulting RFLP fragments for a portion of the *M. tuberculosis* katG gene. Restriction maps for wild-type (W+) and the 264 A→T mutant are shown.

It was further found that the RFLP patterns produced by a MspI digest of the *M. tuberculosis* DNA fragment katG 904–1523 (FIG. 8, lanes B–S) are specific for *M. tuberculosis* and thus allow selective detection of *M. tuberculosis*. MspI digestion of any *M. tuberculosis* katG gene fragment containing the MspI restriction sites depicted in FIG. 5 is expected to yield a similar *M. tuberculosis*-specific RFLP pattern. In contrast, MspI digestions of DNA samples containing other microorganisms, such as mycobacteria other than *M. tuberculosis* (MOTT), yield either different, distinguishable RFLP patterns, or no detectable restriction fragments at all.

When oligonucleotide primers, preferably katG904 and katG1523, are used in a PCR to generate the 620 base pair *M. tuberculosis* DNA amplicon katG 904–1523 in a sample that contains *M. tuberculosis*, typically the PCR yields no amplicon at all for non-*M. tuberculosis* samples (i.e., the primers do not function to create an amplified product). Thus, the generation of the katG 904–1523 amplicon itself is indicative of the presence of *M. tuberculosis* in the sample. Subsequent enzymatic digestion of the amplicon, preferably using restriction endonuclease MspI, can be used to confirm the determination of *M. tuberculosis*.

The present invention will be further described by reference to the following detailed examples. The 58 clinical strains of *Mycobacterium tuberculosis* used in Examples 1 and 2 were obtained from the Mycobacteriology Laboratory at the Mayo Clinic, Rochester, Mo., and the 17 *M. tuberculosis* DNA preparations were obtained from the GWL Hansen's Disease Center, Louisiana State University, Baton Rouge, La. The strain designated H37Rv MC has been maintained at the Mayo Clinic for over 50 years, and therefore was isolated before INH became available as a treatment modality for tuberculosis (circa 1952). H37Rv was deposited in the American Type Tissue Collection, Rockville, Md. in 1937 by A. Karlson of the Mayo Clinic under the accession number ATCC 25618, and has been freely available to the scientific community since. An apparent variant of this strain is disclosed in PCT WO 93/22454 (SEQ ID NO:2, herein). The ATCC strains 27294 and 25618 were recovered from the same patient in 1905 and 1934, respectively. All clinical *M. tuberculosis* strains were confirmed as *M. tuberculosis* using routine identification techniques described by J. A. Washington, "Mycobacteria and Norcardia," in: *Laboratory Procedures in Clinical Microbiology,* 2d ed., Springer-Verlag, N.Y. (1985) at pages 379–417.

For the 15 *M. tuberculosis* strains for which complete katG DNA sequencing was performed, susceptibility testing was done at the Mayo Clinic using Middlebrook 7H11 agar (DiMed, Inc., St. Paul, Minn. 55113) and the 1% proportion method described in *Manual of Clinical Microbiology,* 5th ed., A. Balows et al., eds., *Amer. Soc. Microbiol.* (1991) at pages 1138–52. The same method was used at the Mayo Clinic to determine susceptibility for an additional 43 *M. tuberculosis* strains for which restriction fragment length polymorphisms (RFLP) were determined. Isoniazid concentrations tested using this method included: 0.12, 0.25, 1.0, 2, 4, 8, 16, 32 μg/ml for the 15 strains sequenced and 1.0 and 4.0 μg/ml for the remaining 45 strains. Isoniazid resistance was defined as a maximum inhibitory concentration ($IC_{min}$) ≧1.0 μg/ml. Susceptibility testing was performed elsewhere for an additional 17 *M. tuberculosis* strains for which DNA lysates were provided by Diana L. Williams, Baton Rouge, La. These strains were of diverse geographical origin. 10 of these 17 strains, originated from Japan. The remaining 7 *M. tuberculosis* INH resistant strains included multiple drug resistant strains from recent multiple drug resistant tuberculosis (MDR-TB) nosocomial epidemics in New York, N.Y. and Newark, N.J. All were INH resistant ($IC_{min}$≧1.0 μg/ml), and had resistance to at least one other drug. For all strains provided by Williams, the 1% direct proportion method was used, but the concentration of INH tested, and the media used varied as to site.

To conduct a semiquantitative test of catalase activity, *M. tuberculosis* strains were propagated on Lowenstein-Jensen media deeps contained in 20×150 mm screw-capped tubes. One ml of a 30% hydrogen peroxide (EM, Science, Gibbstown, N.Y. 08027) and 10% Tween 80 (Aldrich Chemical Co., Milwaukee, Wis. 53233) solution mixed in a 1:1 ratio was applied to the surface of growth. After 5 minutes, the highest (mm) of the column of bubbles ($O_2$) generated was recorded.

EXAMPLE 1

DNA Isolation and Polymerase Chain Reaction

A. DNA Isolation

For *M. tuberculosis* strains obtained from Mayo Clinic samples, DNA was extracted from cells using phenol (Boehringer Mannheim, Indianapolis, Ind. 46250-0414) and TE (1.0 M Tris HCI pH 8.0, 0.1M EDTA, Sigma, St. Louis, Mo. 63778) in a ratio of 600 μl:400 μl and 0.1 mm zirconium beads (Biospec Products, Bartlesville, Okla. 74005). The mixture was processed in a mini-bead beater for 30 seconds and allowed to stand for an additional 15 minutes. Following a brief centrifugation to sediment the zirconium beads, DNA in the supernatant was extracted using the IsoQuick kit (MicroProbe Corp., Garden Grove, Calif. 92641).

B. PCR Using Primer Pairs A1–A4 and B1–B2

The DNA sequence for katG (EMBL no. X6808124) employed to design primers is depicted in FIG. 1(A–D), lower strand. The PCR method of R. K. Saiki et al., *Science,* 239, 487 (1988) was used to amplify the katG gene (ca. 2220 base pairs) in two segments which were designated A and B. Genomic DNA preparations (2 μl) were used with primers A1 (5' TCGGACCATAACGGCTTCCTGTTGGACGAG 3') (SEQ ID NO:3) and A4 (5' AATCTGCTTCGCCGACGAGGTCGTGCTGAC 3') (SEQ ID NO:4) or B1 (5' CACCCCGACGAAATGGGACAACAGTTTCCT 3') (SEQ ID NO:5) and B2 (5' GGGTCTGACAAATCGCGCCGGGCAAACACC 3') (SEQ ID NO:6).

The PCR mixture (50 μl) contained 10 mM TRIS, pH 8.3, 50 mM KCI, 1.5 mM $MgCl_2$,0.2 mM each of dATP, dTTP, dGTP, dCTP, 1 μM of each primer pair, 10% glycerol, 1.25 units/50 μl AmpliTaq DNA polymerase (Perkin Elmer Cetus). The mixture was overlaid with mineral oil and subjected to 4 min at 95° C. followed by 50 cycles of 1 min at 94° C. and 2 min at 74° C. A 1495 base pair product from the first half of katG was generated from the A1–A4 primers and 1435 base pair product was generated with the B1–B2 primer pair.

EXAMPLE 2

DNA Sequencing and Homology Analysis

The polymerase chain reaction (PCR) products were prepared for sequencing using the Magic™ PCR Preps DNA Purification System (Promega Corp., Madison, Wis. 53711). The DNA sequences were determined in both directions using the Taq dye-deoxy terminator cycle sequencing kit and 373A DNA sequencer (Applied Biosystems, Foster City, Calif. 94404) using a series of internal sequencing primers which provided appropriate coverage of katG.

The sequence data were analyzed using version 7 of the Genetics Computer Group sequence analysis software, as disclosed by J. Devereux et al., *Nucl. Acids Res.,* 12, 387 (1984). From the 15 *M. tuberculosis* DNA sequences, a consensus sequence was derived to which all *M. tuberculosis* strains were compared. This consensus sequence is depicted in FIG. 1(A–D) (SEQ ID NO:1) as the upper strand, and is compared to the sequence for katG (EMBL no. X6808124), depicted as the lower strand. The two sequences have 98.6% identity, as determined by the GCG program BESTFIT. The DNA sequence data has been submitted to Gen Bank and can be referenced by the accession numbers UO6262 (H37Rv MC), UO6258 (ATCC 25618), UO6259 (ATCC 27294), UO6260 (G6108), UO6261 (H35827), UO6270 (L6627-92), UO6271 (L68372), UO6264 (L11150), UO6268 (L24204), UO6269 (L33308), UO6265 (Li6980), UO6266 (L1781), UO6272 (TMC306), UO6263 (L10373), and UO6267 (L23261). An updated, more complete and accurate *M. tuberculosis* katG gene sequence is presented in FIG. 7(A–C) (SEQ ID NO:20).

The DNA data was then translated, aligned for comparison and a consensus amino acid sequence was generated (FIG. 2) (SEQ ID NO:7). The consensus amino acid sequence (SEQ ID NO:21) generated from the DNA of SEQ ID NO:20 is also presented in FIG. 7.

In general, the overall sequence agreement between INH sensitive and resistant strains was very high; the only deviations are those shown in Table 3.

TABLE 3

Analysis of Catalase-Peroxidase (katG) Gene in *M. tuberculosis* Strains

| Strain | INH MIC[a] (μg/ml) INH | Catalase | Amino Acid Codon[b] 2 | 10 | 17 | 90 | 224 | 243 | 264 | 315 | 337 | 424 | 463 | 505 | 550 | 609 |
|---|---|---|---|---|---|---|---|---|---|---|---|---|---|---|---|---|
| H37Rv MC | <0.12 | 20 | | | | | | | | | | | | | | |
| ATCC 25618 | <0.12 | 12 | | | | | | | | | | | | | | |
| ATCC 27294 | 0.12 | 28 | P–S | | S–N | Q–E | A–S | | | | | | | | A–D | |
| G6108 | <0.12 | 12 | | | | | | | | | | | | | | M–I |
| H35827 | 0.25 | 14 | | | | | | | | | | | | | | |
| L6627-92 | 0.5 | 13 | | | | | | | | | | | | | | |
| L68372 | 1 | 8 | | | | | | | | | Y–C | | R–L | | | |
| L11150 | 8 | 28 | | | | | | | | | | | | | | |
| L24204 | 8 | 36 | | | | | | | | S–T | | | R–L | | | |
| L33308 | 8 | 15 | | | | | | | | | | | | | | |
| L16980 | 16 | 15 | | | | | | | | S–T | | | R–L | | | |
| L1781 | 32 | 5 | | | | | | | A–T | | | | R–L | | | |
| TMC 306 | >32 | 5 | | | | W*[c] | | | | | | | | | | |
| L10373 | >32 | 5 | | 8 bpd[d] | | | | | | | | A–V | | | A–D | |
| L23261 | >32 | 5 | | | | | | | | | | | R–L | W–R | | M–I |
| | | Consensus | P | | S | W | Q | A | A | S | Y | A | R | W | A | M |

[A]MIC denotes Maximum Inhibitory Concentration, INH denotes isoniazid

[B]A denotes alanine, C cysteine, D aspartic acid, E glutamic acid, F phenylalanine, G glycine, I isoleucine, K lysine, L leucine, M methionine, N asparagine, P proline, Q glutamine, R arginine, S serine, T threonine, V valine, W tryptophan, Y tryosine, B bpd B base pair deletion

[c]TGG→TGA( W→stop codon)

[d]8 base pair deletion corresponding to wild type coordinates 98–105 creates a new TAG stop codon beginning 11 bp from coordinate 97.

The data in Table 3 show that six strains, H37Rv MC, ATCC 25618, H35827, L6627-92, L11150, and L33308, are completely homologous to the consensus at the indicated sites. Four are INH sensitive (INH $IC_{min}$<1.0 μg/ml) and two are INH resistant ($IC_{min}$≧1.0 μg/ml). All other strains listed in Table 3 had 1 to 5 differences with the consensus and there was no strong correlation between the number of differences and INH sensitivity.

In the group of INH resistant strains, the most frequent change observed was the conversion of arginine at codon 463 to leucine. This was detected in five of nine isolates examined. There was not a consistent correlation between the loss of catalase activity and INH resistance since strains L11150 and L24204 had high levels of enzymatic activity, yet were INH resistant. Moreover, several other INH resistant strains showed catalase activity near the mean activity (16.5 mm) of the sensitive strains. Two other isolates had lost the ability to make normal katG gene product due either to an eight bp deletion (L10373, semiquantitative catalase, 3mm) or a nonsense mutation (TMC 306, semiquantitative catalase 5 mm). It was not possible to determine if, or how, any of the deviations from the consensus reported in Table 3 affect catalase activity or cause INH resistance. However, the change at codon 463 is frequent enough that is indicative of resistance.

The DNA sequence analysis indicated that the codon 463 occurs in the context of an NciI-MspI restriction site (both enzymes recognize the same site). Thus, when in the wild type sequence depicted in FIG. 1 at bases 1455–1458, CC GGG, is changed to CCTGG, it is no longer recognized (or cleaved) by either of these enzymes. The 1435 bp amplicon produced from the half of katG gene containing codon 463 normally has five NciI-MspI restriction sites whereas the codon altered strains have only four sites, as shown in FIG. 3. The loss of the site in question causes a unique restriction fragment length polymorphism (RFLP), which can be readily adapted to assay for resistant strains, as described in Example 3, below.

EXAMPLE 3

RFLP Analysis: MspI-NciI site in Codon 463

For restriction fragment length polymorphism (RFLP) analysis, a 1435 base pair amplimer (produced using the B1–B2 primers) representing the 3' half of the katG gene was generated using PCR and then digested with NciI or MspI (Sigma Chemical Co., St. Louis, Mo. 63178). The gene fragments were analyzed with agarose gel electrophoresis using 2% Metaphor agarose (FMC BioProducts, Richland, Me. 04811). The gel was stained with ethidium bromide and photographed. The investigator who performed all restriction digests and electrophoresis was blinded as to the INH $IC_{min}$ results.

Figure 4:
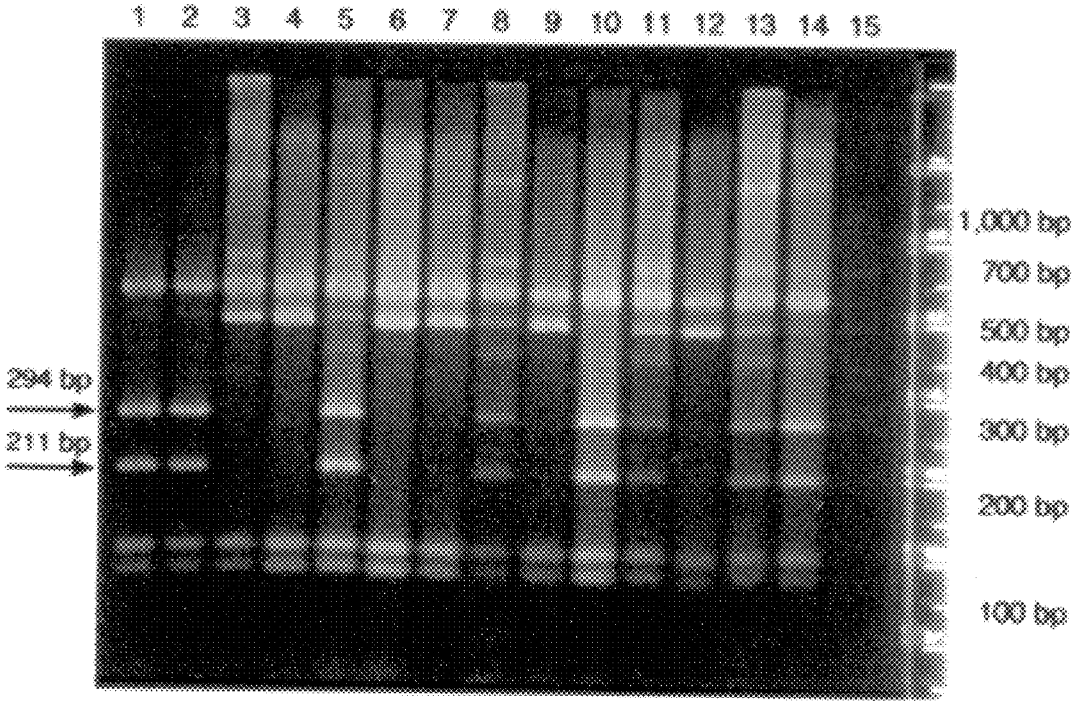
FIG. 4 depicts the results of a gel electrophoresis of the NciI digest of the part B amplicon of 14 strains of *M. tuberculosis* (1–14).

The results of this experiment are depicted in FIG. 4, wherein Lane 1 denotes strain H37Rv MC, $IC_{min}$=<0.12 μg/ml; (2) L6627-92, 0.5 μg/mL; (3) L68372, 1.0 μg/ml; (4) L16980, 16 μg/mL; (5) L39791, 16 μg/mL; (6) L1781, 32 μg/mL; (7) L9118, 4 μg/mL; (8) L11150, 8 μg/mL; (9) L24204, 8 μg/mL; (10) L68858,<0.12 μg/mL; (11) 1115A<0.12 μg/mL; (12) L23261,>32 μg/mL; (13) 1341, >32 μg/mL; (14) M10838,>32 μg/mL; (15) molecular weight standard: PCR markers (United States Biochemical Corp., Cleveland, Ohio 44122). The digests obtained from resistant strains can be readily visually detected and differentiated from digests from susceptible strains.

Subsequently, a total of 75 *M. tuberculosis* strains (including the 15 strains sequenced) were analyzed for their loss of the appropriate restriction site. Of these strains, 32 were INH sensitive and 43 were INH resistant. The data showed that 19 (44%) of the 43 resistant strains had lost the expected restriction site in codon 463. One of the 33 (2.9%) sensitive strains had lost this restriction sites as well. None of the six sensitive strains listed in Table 3 lost this site.

EXAMPLE 4

Determination of the Presence or Absence of Mutations at Codons 264, 315, 337 or 463 in the *M. tuberculosis* katG Gene A. Materials Primer pairs used for polymerase chain reaction were katG904/katG1523 (nucleotide sequences 5' AGC TCG TAT GGC ACC GGA AC 3' (SEQ ID NO:16) and 5' TTG ACC TCC CAC CCG ACT TG 3' (SEQ ID NO:17)) and katG633/katG983 (nucleotide sequences 5' CGG TAA GCG GGA TCT GGA GA 3' (SEQ ID NO:18) and 5' CAT TTC GTC GGG GTG TTC GT 3' (SEQ ID NO:19)). Subunits thereof that hybridize to the amplified DNA under the conditions described hereinbelow may also be used.

Polyacrylamide was obtained from National Diagnostics, Tris Borate EDTA solution (6X, cat. no. T6400), magnesium chloride, and dithiothreitol (DTT) from Sigma Chemical Company (St. Louis, Mo.), TEMED (cat. no. 161-0800) and ethidium bromide (EtBr) from Biorad, ammonium persulfate from Intermountain Sci., and nucleotides (dATP, dGTP, dCTP and dTTP, 100 mM solutions) from Boehringer Mannheim Biochemicals. dUTP was obtained from Pharmacia. AmpErase™ uracil-N-glycosylase (UNG) and AmpliTaq™ were obtained from Perkin Elmer.

Restriction endonucleases were obtained as follows: MspI from Sigma (cat. no. R-4506) 10 u/μl with blue palette buffer; RsaI from New England Biochemical (cat. no. 167S) 10 u/μl with NEB buffer 1; and CfoI from Promega (cat. no. R624) 10 u/μl with buffer B.

100 mM nucleotide concentrates obtained from Boehringer Mannheim Biochemicals were used to make the dNTP stock solution, which was 1.25 mM in each nucleotide. Specifically, 10 μl each of dATP, dGTP, dCTP, and dTTP concentrates were added to 760 μl water. dNTP(U) stock solution, also 1.25 mM in each nucleotide, was made from the same 100 mM dATP, dGTP and dCTP concentrates, and 100 mM dUTP concentrate from Pharmacia. Ten μl of each of the four concentrates was added to 760 μl water to make the stock solution.

10X PCR buffer consisted of 100 mM Tris, pH 8.3, 500 mM KCl, and 15 mM MgCl2. PCR mix "A" consisted of 1X PCR buffer, 200 μM each dATP, dGTP, dCTP, and dUTP, 1 μM each katG904 (SEQ ID NO:16) and katG1523 (SEQ ID NO: 17) primers, 10% glycerol, 10 units/ml AmpErase™UNG, and 0.025 units/μl AmpliTaq. PCR mix B consisted of 1X PCR buffer, 200 μM each dATP, dGTP, dCTP, and dTTP, 1 μM each katG904 (SEQ ID NO:16) and katG1523 (SEQ ID NO:17) primers, 10% glycerol, and 0.025 units/μl AmpliTaq. PCR mix "C" consisted of 1X PCR buffer, 200 μM each dATP, dGTP, dCTP, and dUTP, 1 μM each katG633 (SEQ ID NO:18) and katG983 (SEQ ID NO:19) primers, 10% glycerol, 10 units/ml AmpErase™UNG, and 0.025 units/μl AmpliTaq.

Gel loading solution (Blue Juice) was obtained from Sigma (cat. no. G2526). Gels were photographed on a UV transilluminator (UVP) with Polaroid 667 black and white film (3¼X 4¼ inch) through an orange filter.

DNA extracts (target DNA) were prepared as described in Example 1(A).

B. MspI RFLP analysis

PCR was performed by adding 2 μl of DNA extract to 48 μl PCR mix "A." Each reaction was covered with 2 drops of mineral oil. Temperature was cycled (Perkin Elmer DNA Thermo Cycler model 480) for 1 cycle of (5'–37°; 5'–95°) and 40 cycles of (1'–94°; 0.5'–60°; 0.75'–72°) and a 72° soak. MspI (10 u/μl) was diluted 1:10 in 100 mM $MgCl_2$. The amplified DNA (base pairs 904 through 1523) of a wild-type katG gene contains 7 MspI restriction sites (FIG. 5); of the 8 fragments produced in an MspI restriction digest, 4 are of sufficient length to be visualized using gel electrophoresis (see FIG. 5 for a restriction map). Diluted MspI (1 μl) was mixed with 9 μl of the PCR reaction mixture containing the amplified DNA. The digest was incubated at 37° C. for 2 hours, then heated to 65° C. for 10 minutes. Subsequently, 10 μl of the digest plus 4 μl blue juice was electrophoresed on 6% polyacrylamide for 0.4 hour at 200 V. The gel was stained in EtBr (0.5 mg/ml 1XTBE) for 5 minutes and photographed.

Figure 8:
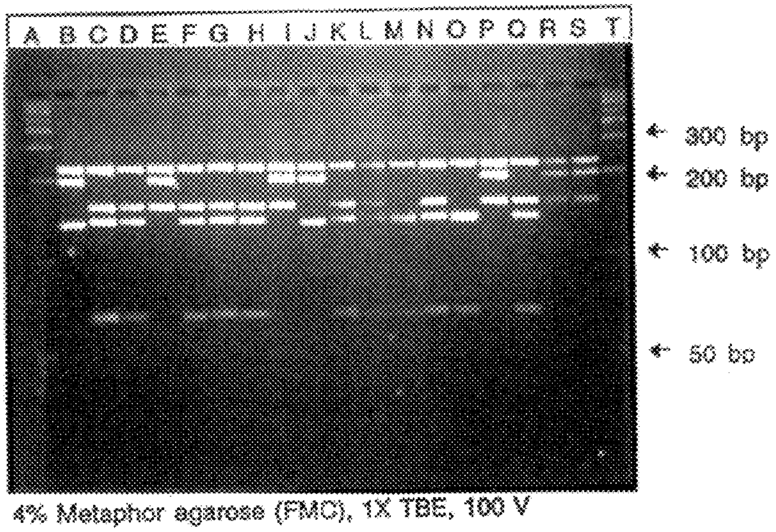
FIG. 8 depicts the RFLP patterns produced by an MspI restriction digest of an amplified portion of the DNA of the katG genes of wild-type and mutant strains of *M. tuberculosis*, wherein the mutant DNA contains mutations at either codon 315 or codon 463, or both.

Results are shown in FIG. 8. Lanes C, D, F, G, H, K, L, N, and Q show the wild-type genotype at codons 315 (AGC) and 463 (CGG) evidenced by 4 restriction of sufficient length to be visualized using gel electrophoresis (228, 153, 137, and 65 base pairs, respectively, see FIG. 5). Lanes M and 0 show an RFLP indicating a mutation at codon 315 that adds a new MspI restriction site, causing the 153 base pair fragment to be shortened to 132 base pair and become difficult to resolve from the 137 base pair fragment. The resulting 3 fragment pattern (65, 132/137 and 228 base pair) is indicative of an INH resistant strain. Lanes E, I and P show an RFLP indicating a mutation at codon 463 that eliminates an MspI restriction site, evidenced by the 3 visible fragments produced by cleavage versus the 4 produced by the wild-type genotype. The resulting 3 fragment pattern (153, 202, and 228 base pair) is indicative of an INH resistant strain. Lanes B and J show an RFLP indicating mutations at both codon 315 and codon 463. The resulting gain and loss of MspI restriction sites produces a distinctive 3 fragment RFLP pattern (132, 202 and 228 base pair) indicative of an INH resistant strain (see FIG. 5 for a restriction map).

C. RsaI RFLP analysis

PCR was performed by adding 2 μl of DNA extract to 48 μl PCR mix "B." Each reaction was covered with 2 drops of mineral oil. Temperature was cycled (Perkin Elmer DNA Thermo Cycler model 480) for 1 cycle of 2 minutes at 94° and 40 cycles of (1'–94°; 0.5'–60°; 0.75'–72°) and a 4° soak. RsaI (10 u/μl) was diluted 1:20 in 100 mM $MgCl_2$/100 mM dithiothreitol. The amplified DNA (bases 904 through 1523) of a wild-type katG gene contains 2 RsaI restriction sites. Diluted RsaI (2 μl) was placed on top of the PCR reaction mixture (on the oil) and centrifuged at about 12,000×g for 10 seconds to drop the RsaI enzyme into the mixture containing the amplified DNA. The resulting mixture was incubated overnight (15–20 hours) at 37°, after which 10 μl of the digest plus 1 μl blue juice was electrophoresed on 6% polyacrylamide for 0.4 hour at 200 V. The gel was stained in EtBr (0.5 mg/ml 1XTBE) for 5 minutes and photographed.

Figure 9:
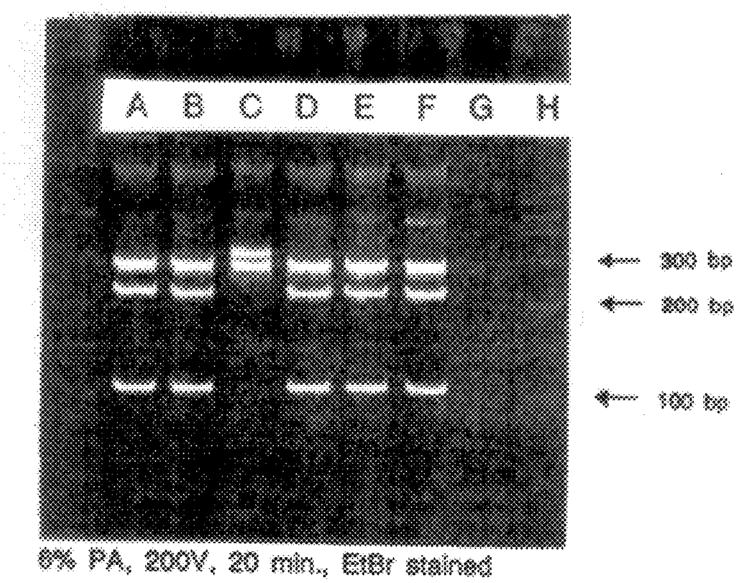
FIG. 9 depicts the RFLP patterns produced by an RsaI restriction digest of an amplified portion of the DNA of the katG genes of wild-type and mutant strains of *M. tuberculosis*, wherein the mutant DNA contain a mutation at codon 337.

Results are shown in FIG. 9. Lanes A, B, D, E, and F show the wild-type genotype at codon 337 (TAC), evidenced by three restriction fragments produced by cleavage at two sites. Lane C shows an RFLP indicating a mutation at codon 337 that eliminates one of the RsaI restriction sites. The resulting two fragment pattern has been observed in an INH resistant strain.

D. CfoI RFLP analysis.

PCR was performed by adding 2 μl of DNA extract to 48 μl PCR mix "C." Each reaction was covered with 2 drops of mineral oil. Temperature was cycled (Perkin Elmer DNA Thermo Cycler model 480) for 1 cycle of (5'–37°; 5'–95°) and 40 cycles of (1'–94°; 0.5'–60°; 0.75'–72°) and a 72° soak. The amplified DNA (bases 633 through 983) of a wild-type katG gene contains 3 CfoI restriction sites. CfoI (10 u/μl) was diluted 1:5 in 100 mM $MgCl_2$. Diluted CfoI (1 μl) was mixed with 9 μl of the PCR reaction mixture containing the amplified DNA. The digest was incubated at 37° for 2 hours, then heated to 65° C. for 10 minutes. Subsequently, 10 μl of the digest plus 4 μl blue juice was electrophoresed on 6% polyacrylamide for 0.4 hour at 200 V. The gel was stained in EtBr (0.5 mg/ml 1XTBE) for 5 minutes and photographed.

Figure 10:
FIG. 10 depicts the RFLP patterns produced by a CfoI restriction digest of an amplified portion of the DNA of the katG genes of wild-type and mutant strains of *M. tuberculosis*, wherein the mutant DNA contains a mutation codon 264.

Results are shown in FIG. 10. Lanes A–C show the wild-type genotype at codon 264 (GCG), evidenced by 4 restriction fragments produced by cleavage at three sites. Lane E shows an RFLP indicating a mutation at codon 264 that eliminates one of the CfoI restriction sites. The resulting three fragment pattern has been observed in an INH resistant strain.

EXAMPLE 5

Rapid Simultaneous Detection of *M. tuberculosis* (MTB) and Determination of Isoniazid (INH) Susceptibility Directly from Sputum Five microliter aliquots of 785 ethanol-fixed sputum samples from 365 patients were screened for MTB and INH resistance using the MspI RFLP analysis disclosed in Example 4(B). Primers katG904 (SEQ ID NO:16) and katG1523 (SEQ ID NO:17) were used in a polymerase chain reaction as described in Example 4 to produce a 620 base pair katG gene fragment or "amplicon" (base pairs 904 through 1523), which was digested with MspI. The resulting restriction fragment pattern was visualized using gel electrophoresis. A result considered "positive for MTB" was defined as production of a katG amplicon that generated an RFLP pattern (see FIG. 8) indicative of wild-type MTB or mutant MTB (MTB containing a S315T or R463L mutation, or both, in the 620 base pair katG amplicon). A negative result was defined as the failure to produce a katG amplicon (i.e., failure to produce the 620 base pair segment in the PCR), or, in rare cases, the production of a katG amplicon followed by generation of an RFLP pattern that differed from the RFLP pattern know to be associated with wild-type or mutant (S315T, R463L or S315T/R463L) MTB.

The results of this PCR-RFLP assay were compared to results for acid-fast bacilli (AFB) staining by the Ziehl-Neelsen method, and to results of culture and INH susceptibility testing using the BACTEC radiometric method. Technologists performed PCR-RFLP after AFB bacilli stains and cultures were done, and were blinded to the results for AFB stains and cultures. Patient charts were also reviewed for clinical correlation.

Seventy of 785 (8.9%) sputa were AFB stain-positive. MTB was cultured from 48 of these 70 samples. For 9 other AFB stain-positive samples, MTB was not isolated, however MTB was isolated from these same patients from a recent prior sputum. Eight of these 9 patients were receiving antituberculous therapy at the time the sputum was collected for the study.

Mycobacteria other than MTB (MOTT) were exclusively cultured from 9 other AFB stain-positive specimens [*M. avium intracellulare* (6), *M. fortuitum* (2), *M. kansasii* (1)]. No mycobacteria (MTB or MOTT) were cultured from 2 AFB stain-positive sputa obtained from two patients whose recent prior sputa did not grow mycobacteria. No clinical laboratory information (including whether prior cultures for mycobacteria were done) was available for the 2 remaining AFB stain-positive but culture-negative sputa.

The results for the PCR-RFLP were positive for MTB for 45 of the 48 AFB stain-positive samples that grew MTB. Two of these 3 discordant samples had few AFB on stain and 1 had rare AFB on stain. Additional 5 microliter aliquots from these 3 discordant samples were tested and produced positive results for PCR-RFLP. For the 9 samples that were AFB stain-positive, MTB culture-negative, and where recent prior samples from the same patient were MTB culture-positive, PCR-RFLP results were positive for MTB. In no case was a katG amplicon generated for the 9 samples from which MOTT were recovered on culture. PCR-RFLP results were also negative for MTB for the 4 remaining AFB stain-positive, culture-negative samples.

For AFB stain-positive samples from which MTB was isolated and for which susceptibility testing was performed (n=45), 7 isolates (15.6%) were INH resistant. All of these INH resistant isolates were detected by the PCR-RFLP and analysis of the RFLP pattern showed them to carry the S315T mutation. These 7 isolates were from 7 different patients and 4 had different susceptibility patterns for other drugs.

The PCR-RFLP method produced a katG amplicon for 39 of the 715 AFB stain-negative samples. MTB was cultured from only 3 of these samples. However, for 21 of the 39 samples, although MTB was not cultured, MTB was recovered from recent prior samples from the same patient and/or the patient was receiving antituberculous therapy at the time the study sample was collected. Comprehensive clinical and laboratory chart reviews were not available for the remaining 15 patients.

This PCR-RFLP MTB katG assay, which can be performed in one working day, is thus a reliable, rapid method for detecting MTB and determining INH susceptibility directly from AFB stain-positive sputa.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for selectively detecting *M. tuberculosis* in a sample containing DNA, said method comprising amplifying the DNA to generate a detectable amount of amplified DNA comprising a katG DNA fragment consisting of base 904 through 1523 of the *M. tuberculosis* katG gene as depicted in FIG. 7 (SEQ ID NO:20), wherein the generation of the katG DNA fragment is indicative of the presence of *M. tuberculosis* in the sample.

2. The method of claim 1 wherein the DNA is amplified in a polymerase chain reaction using oligonucleotide primer katG904 (SEQ ID NO:16) and oligonucleotide primer katG1523 (SEQ ID NO:17).

3. The method of claim 1 wherein the katG DNA fragment comprises a restriction site comprising either a G or a C at the nucleotide position occupied by base 1013 in codon 315 of the *M. tuberculosis* katG gene as depicted in FIG. 7 (SEQ ID NO:20), said method further comprising:

contacting the katG DNA fragment with a restriction endonuclease that cleaves either at said restriction site comprising a G at the nucleotide position occupied by base 1013 of codon 315, or at said restriction site comprising a C at the nucleotide position occupied by base 1013 of codon 315, but not at both of said restriction sites, to yield at least one cleaved fragment;

electrophoresing the at least one cleaved fragment to yield an electrophoretic mobility pattern comprising the at least one cleaved fragment; and analyzing the mobility pattern to selectively detect the presence of *M. tuberculosis* in the sample.

4. The method of claim 3 wherein the restriction endonuclease is MspI.

5. The method of claim 3 wherein the electrophoresis comprises gel electrophoresis, and wherein the presence of *M. tuberculosis* in the sample is selectively detected using restriction fragment length polymorphism (RFLP) analysis of said electrophoretic mobility pattern.

6. The method of claim 1 wherein the sample is a biological fluid.

7. The method of claim 6 wherein the biological fluid is human sputum.

8. The method of claim 1 further comprising determining whether or not the katG DNA fragment has a S315T mutation, wherein the presence of a S315T mutation is indicative of an INH-resistant strain of *M. tuberculosis.*

9. The method of claim 8 wherein the katG DNA fragment comprises a restriction site comprising either a G or a C at the nucleotide position occupied by base 1013 in codon 315 of the *M. tuberculosis* katG gene as depicted in FIG. 7 (SEQ ID NO:20), and wherein the step of determining whether or not the katG DNA fragment has a S315T mutation comprises contacting the katG DNA fragment with a restriction endonuclease that cleaves either at said restriction site comprising a G at the nucleotide position occupied by base 1013 of codon 315, or at said restriction site comprising a C at the nucleotide position occupied by base 1013 of codon 315, but not at both of said restriction sites, to yield at least one cleaved fragment, and wherein cleavage at said restriction site is indicative of either the presence or the absence, but not both, of a S31 ST mutation in the katG DNA fragment.

10. The method of claim 9 wherein the restriction endonuclease is MspI, and wherein cleavage at said restriction site is indicative of the presence of a S315T mutation in the katG DNA fragment.

11. The method of claim 9 further comprising electrophoresing the at least one cleaved fragment to yield an electrophoretic mobility pattern comprising the at least one cleaved fragment; and analyzing the mobility pattern to determine the presence or absence of a S315T mutation in the katG DNA fragment.

12. The method of claim 11 wherein the electrophoresis comprises gel electrophoresis, and wherein the presence of *M. tuberculosis* in the sample is selectively detected using restriction fragment length polymorphism (RFI,P) analysis of said electrophoretic mobility pattern.

13. A method for selectively detecting *M. tuberculosis* in a sample containing DNA, said method comprising:

(a) amplifying the DNA to generate a detectable amount of amplified DNA comprising a katG DNA fragment comprising base 904 through 1523 of the *M. tuberculosis* katG gene, wherein the katG DNA fragment further comprises a restriction site comprising either a G or a C at the nucleotide position occupied by base 1013 in codon 315 of the *M. tuberculosis* katG gene as depicted in FIG. 7 (SEQ ID NO:20);

(b) contacting the katG DNA fragment with a restriction endonuclease that cleaves either at said restriction site comprising a G at the nucleotide position occupied by base 1013 of codon 315, or at said restriction site comprising a C at the nucleotide position occupied by base 1013 of codon 315, but not at both of said restriction sites, to yield at least one cleaved fragment;

(c) electrophoresing the at least one cleaved fragment to yield an electrophoretic mobility pattern comprising the at least one cleaved fragment; and (d) analyzing the mobility pattern to selectively detect the presence of *M. tuberculosis* in the sample.

14. The method of claim 13 wherein the restriction endonuclease is MspI.

15. The method of claim 13 wherein the sample is a biological fluid.

16. The method of claim 15 wherein the biological fluid is human sputum.

17. The method of claim 13 wherein the electrophoresis comprises gel electrophoresis, and wherein the presence of *M. tuberculosis* in the sample is selectively detected using restriction fragment length polymorphism (RFLP) analysis of said electrophoretic mobility pattern.

18. A method for selectively detecting *M. tuberculosis* in a sample containing DNA, said method comprising:

(a) amplifying the DNA to generate a detectable amount of amplified DNA comprising a katG DNA fragment comprising base 904 12through 1523 of the *M. tuberculosis* katG gene as depicted in FIG. 7 (SEQ ID NO:20);

(b) contacting the katG DNA fragment with a restriction endonuclease that cleaves at C/CGG to yield at least one cleaved fragment;

(c) electrophoresing the at least one cleaved fragment to yield a mobility pattern comprising the at least one cleaved fragment; and (d) analyzing the mobility pattern to selectively detect the presence of *M. tuberculosis* in the sample.

19. The method of claim 18 wherein the restriction endonuclease is MspI.

20. The method of claim 18 wherein the sample is a biological fluid.

21. The method of claim 20 wherein the biological fluid is human sputum.

22. The method of claim 18 wherein the electrophoresis comprises gel electrophoresis, and wherein the presence of *M. tuberculosis* in the sample is selectively detected using restriction fragment length polymorphism (RFLP) analysis of said electrophoretic mobility pattern.

* * * * *

UNITED STATES PATENT AND TRADEMARK OFFICE

CERTIFICATE OF CORRECTION

PATENT NO.: 5,922,575
DATED: July 13, 1999
INVENTOR(S): Cockerill, III, et al.

It is certified that error appears in the above-identified patent and that said Letters Patent is hereby corrected as shown below:

Column 45, line 35, delete "S31 ST", and insert –S315T–;

Column 45, line 50, delete "(RFI,P)", and insert --RFLP)–; and

Column 46, line 34, delete "12".

Signed and Sealed this

Tenth Day of April, 2001

*Attest:*

NICHOLAS P. GODICI

*Attesting Officer*

*Acting Director of the United States Patent and Trademark Office*